United States Patent [19]

Shanklin, Jr.

[11] Patent Number: 5,198,449
[45] Date of Patent: Mar. 30, 1993

[54] N-SUBSTITUTED ALPHA-ARYLAZACYCLOALKYLMETHANAMINES AND THEIR USE AS CARDIOVASCULAR AGENTS

[75] Inventor: James R. Shanklin, Jr., Richmond, Va.

[73] Assignee: A. H. Robins Company Incorporated, Richmond, Va.

[21] Appl. No.: 515,620

[22] Filed: Apr. 27, 1990

[51] Int. Cl.$^5$ .............. C07D 211/28; A61K 31/445
[52] U.S. Cl. ........................... 514/317; 546/205; 546/174
[58] Field of Search ................ 546/205; 514/317

[56] References Cited

U.S. PATENT DOCUMENTS

| | | | |
|---|---|---|---|
| 3,479,370 | 11/1969 | Lunsford | 260/326.3 |
| 3,489,769 | 1/1970 | Helsley | 260/326.5 |
| 3,576,810 | 4/1971 | Duncan | 260/294 |
| 4,777,176 | 10/1988 | Worthington | 546/205 |

FOREIGN PATENT DOCUMENTS 1517934  7/1978  United Kingdom .

OTHER PUBLICATIONS

E. K. Orlova et al., Khim.-Farm. Zh. 1979, 13(1), 47–51 (Russ) CA90:168416x.
Hesley et al., J. Med. Chem., 11, 472–475 (1968).
Helsley et al., J. Med. Chem., 12, 1098–1100 (1969).
Duncan et al., J. Med. Chem., 13, 1–6 (1970).

Primary Examiner—David B. Springer
Attorney, Agent, or Firm—Walter Patton

[57] ABSTRACT

Novel compounds of the formula below wherein W is azetidine, pyrrolidine or piperidine, Q is a straight chain hydrocarbon radical of 1–4 carbons and may contain a double bond, and

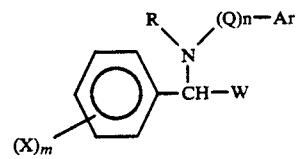

Ar is phenyl, pyridinyl or pyrimidinyl, a process for their preparation, and novel intermediates are disclosed. The novel compounds and the pharmaceutical compositions of this invention are useful in the treatment of hypertension, arrhythmias and angina.

4 Claims, No Drawings

N-SUBSTITUTED ALPHA-ARYLAZACYCLOALKYLMETHANAMINES AND THEIR USE AS CARDIOVASCULAR AGENTS

BACKGROUND OF THE INVENTION

1. Field of Invention

Novel N-substituted-α-arylazacycloalkylmethanamines compounds useful in treating certain cardiovascular disorders, novel intermediates thereto, and a novel process for the preparation of these compounds are herein disclosed.

2. Information Disclosure Statement

Four compounds similar to the compounds of the present invention have been reported. Compounds 1 and 2 are reported in *Khim.-Farm. Zh.*, 1979, 13(1), 47–51 (CA 90:16841x) as having neurotropic activity.

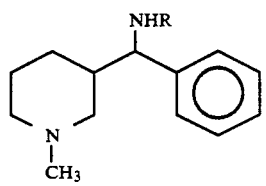

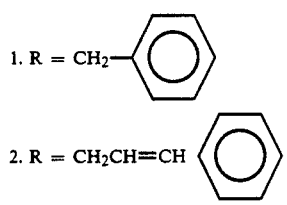

Compound 3 has a Chemical Abstracts registry number (101997-50-6) but no additional information is available.

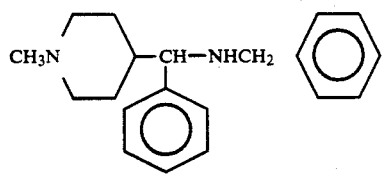

1-Benzhydryl-N-benzyl-α-phenyl-2-azetidmemethanamine 4 is disclosed in the British patent 1,517,934 (and German patent 2,548,053) as being a preferred compound useful in the treatment of mammalian obesity.

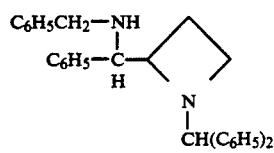

Compounds related to those of the present invention having the formula

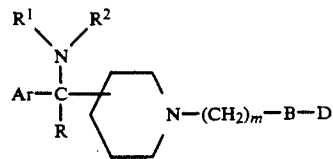

where R is aryl, cycloalkyl or loweralkyl; p is 0 or 1; $R^1$ and $R^2$ are selected independently from H, loweralkyl, phenyl or phenylloweralkyl; B is

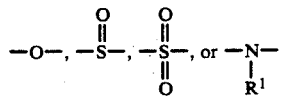

and D is aryl which are useful in treating cardiac disturbances and are also antihistamines and antisecretory agents are the subject of our U.S. application Ser. No. 154,390 filed on Feb. 2, 1988.

SUMMARY OF THE INVENTION

The novel N-substituted-α-phenylazacycloalkylmethanamines of the present invention where the azacycloalkyl group is azetidine, pyrrolidine, or piperidine have the formula

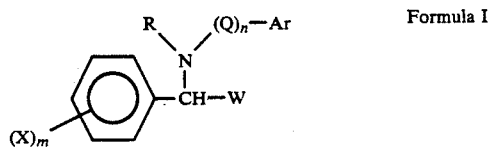

Formula I wherein

R is selected from H, loweralkyl, $R^2C(O)-$, $R^2NHC(O)$, $(R^2)_2NC(O)-$ or $R_2OC(O)-$;

Q is a straight chain hydrocarbon radical of 1–4 carbons and may contain a double bond;

n=0 or 1;

W is

1-$R^1$-2(or 3) azetidinyl

1-$R^1$-2(or 3) pyrrolidinyl, or

1-$R^1$-2(or 3 or 4) piperidinyl;

Ar is

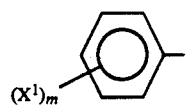

or, when n is 0, can be pyridinyl or 2-pyrimidinyl;

m is 0–2;

X and $X^1$ are independently selected from halogen, loweralkyl, trifluoromethyl, or $-OR^2$;

$R^1$ is selected from hydrogen, loweralkyl, loweralkylene, cycloloweralkyl, loweralkylcycloloweralkyl, $CF_3CH_2-$, or $-(alk)_p-Y$ where p is 0 or 1, Y is $-C(O)NHR^2$, $-C(=NH)NH_2$, phenyl, naphthyl, 2-quinolinyl, 2-pyrimidinyl, 2,4-(1H, 3H)quinazolinedione-3-yl, hydroxy, loweralkoxy, $-O$-loweralkylene, $-O$-aryl (where aryl is phenyl, naphthyl, 2-methoxy-4-acetylphenyl, 4-loweralkylcarbonylphenyl, or 4-loweralkoxycarbonylphenyl), 4-loweralkoxycarbonylphenyl), benzoyl, 4-phenylpiperazine, 3H or 3-loweralkyl-2-oxoimidazolidin-1-yl, 3H or 3-loweralkyl or benzoyl-2-oxobenimidazolidin-1-yl, phthalimide, amino, NHR³ (R³ is —C(=NH)—NH₂, —C(O)NH-loweralkyl or phenyl, 2-pyrimidinyl, phenyl, loweralkylcarbonylphenyl or benzenesulfonyl), benzenesulfonyl, benzenesulfinyl, benzenesulfenyl, —CH(OH)CH₂OC₆H₅, or phenylaminocarbonyl or loweralkylaminocarbonyl; R² is H, loweralkyl, phenyl or phenyl substituted by halogen, loweralkyl, loweralkoxy, trifluoromethyl, loweralkylcarbonyl or diloweralkylaminoloweralkyl; with a proviso that when —(Q)ₙAr is —CH₂C₆H₅ or —CH₂CH=CHC₆H₅, X cannot be H and W cannot be 1-methyl-4-piperidinyl; the stereoisomers thereof and pharmaceutically acceptable acid addition salts.

The term loweralkyl means straight, cyclic and branched chain hydrocarbon radicals of from one to eight carbons including, but not limited to methyl, ethyl propyl, cyclopropyl, isopropyl, butyl, isobutyl, t-butyl, pentyl isopentyl, neopentyl, hexyl, cyclohexyl, heptyl, octyl, isooctyl, and the like.

The term loweralkylene means straight and branched chain hydrocarbon radicals of from 2-6 carbons having one or more double bonds including, but not limited to propylene, butylene; isobutylene and the like.

Loweralkylcycloloweralkyl includes, but is not limited to cyclopropylmethyl, cyclohexylmethyl and the like.

The term halogen means fluorine, chlorine, bromine, and iodine radicals.

The term substituted phenyl refers to a phenyl radical substituted by a radical or radicals such as those under the definitions of X, X¹ and Z.

The term "alk" refers to a hydrocarbon radical, straight or branched, of from 1 to 6 carbons and may include one or more double bonds.

Loweralkoxy refers to an oxygen radical to which a loweralkyl group is attached.

The term stereoisomers includes optical isomers, diasterisomers, and geometric isomers.

The term "pharmaceutically acceptable acid addition salts" includes acid addition salts, solvates, and quaternary salts which are physiologically compatible in warm blooded animals. Acid addition salts may be formed from the pharmaceutically acceptable acids, including but not limited to, hydrochloric hydrobromic, sulfuric, phosphoric, methanesulfonic, fumaric, maleic, succinic, oxalic, citric, hexamic and the like.

The term cardiovascular disorders refers to hypertension, arrhythmias, and angina.

It is an object of this invention to provide novel compounds of Formula I. It is another object to provide a novel process for the preparation of some of the Formula I compounds from which other compounds of Formula I can be prepared.

It is a further object of this invention to provide a method of treating warm blooded animals for hypertension, arrththmias, and angina with compounds of Formula I and a further object to provide a pharmaceutical composition useful in treating hypertension, arrhythmias, and angina. A still further object is to provide novel intermediates to compounds of Formula I.

Formula I compounds of this invention are evaluated for antihypertensive activity in the spontaneously hypertensive rat, for calcium channel blockade in the isolated rabbit aorta preparation, and for angina by measuring changes in coronary arterial blood flow. Compounds which have calcium channel blocking activity, such as the known drug verapamil, would be expected to be useful in treating hypertension and cardiac arrhythmias.

DETAILED DESCRIPTION OF THE INVENTION

The compounds of Formula I are prepared from intermediates having the structure of Formula II.

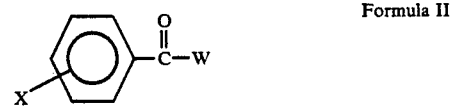

Formula II

Some Formula II compounds and their precursors where W is pyrrolidine or piperidine and X is 4-F, 3-CF₃ or 4-OCH₃ are disclosed in the commonly owned U.S. Pat. Nos. 3,479,370 and 3,489,769 and 3,576,810 and the related publications in J. Med. Chem. 11, 472-475 (1968), J. Med. Chem. 12, 1098-1100 (1969), J. Med. Chem. 13, 1-6 (1970) and J. Med. Chem. 32, 105-118 (1989) which are hereby incorporated by reference. The following methods are illustrative of the preparation of Formula I compounds from Formula II intermediates. In these methods, the azacycloalkyl group W is represented by the 4-piperidinyl group. The group W also includes 2- and 3-azetidinyl, 2- and 3-pyrrolidinyl, and 2- and 3-piperidinyl.

Method A

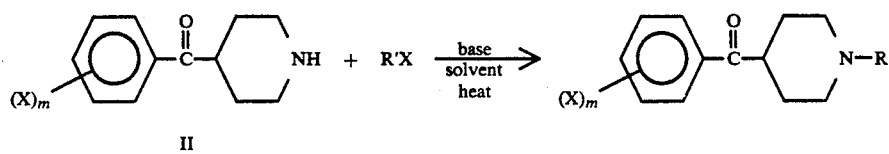

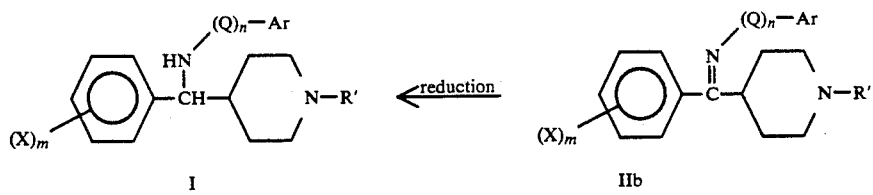

The intermediate II is first alkylated with the desired group R'X, where X is halogen to give the intermediate IIa. Reaction of IIa with the appropriate amine or aniline gives the imine IIb which is reduced under standard conditions with lithium aluminum hydride and the like to obtain the Formula I compound.

Method B, pt. A

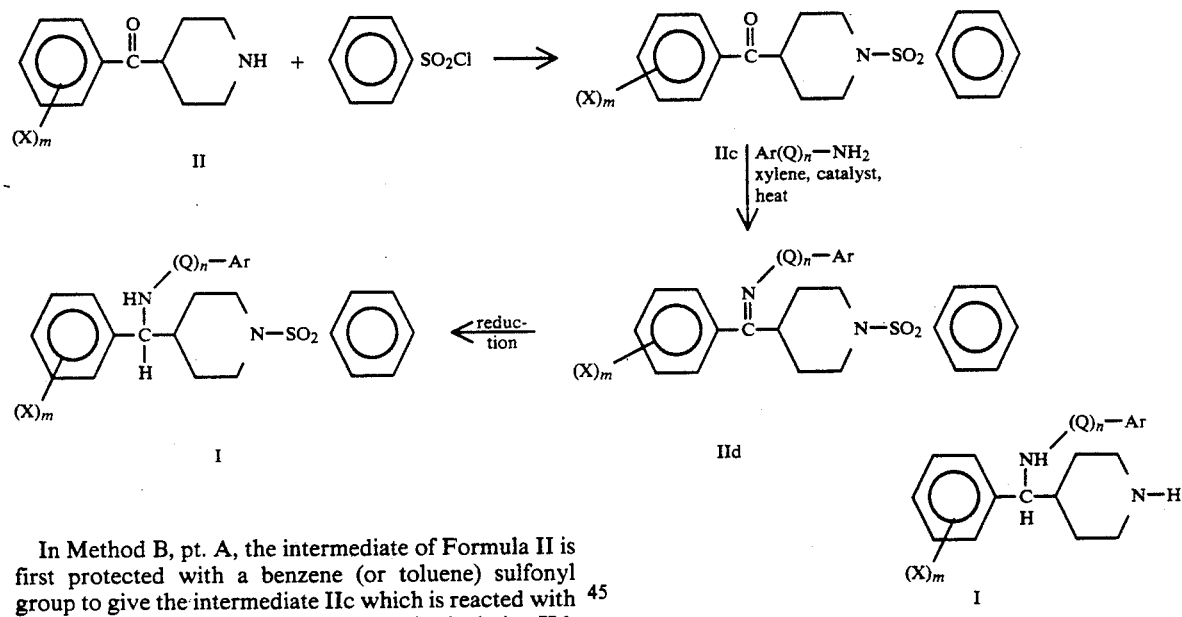

In Method B, pt. A, the intermediate of Formula II is first protected with a benzene (or toluene) sulfonyl group to give the intermediate IIc which is reacted with the appropriate amine or aniline to obtain the imine IId. Reduction as in Method A gives the compound of Formula I where R' is the benzene or toluene sulfonyl group.

Method B, pt. B

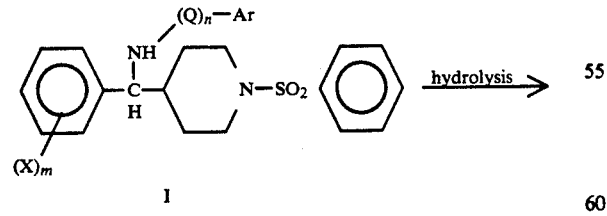

Method B, pt. B discloses removal of the protecting benzene (or toluene) sulfonyl group, preferably in refluxing 48% hydrobromic acid and phenol. Alkylation of the deprotected Formula I compound under the usual conditions gives additional Formula I compounds.

Method C

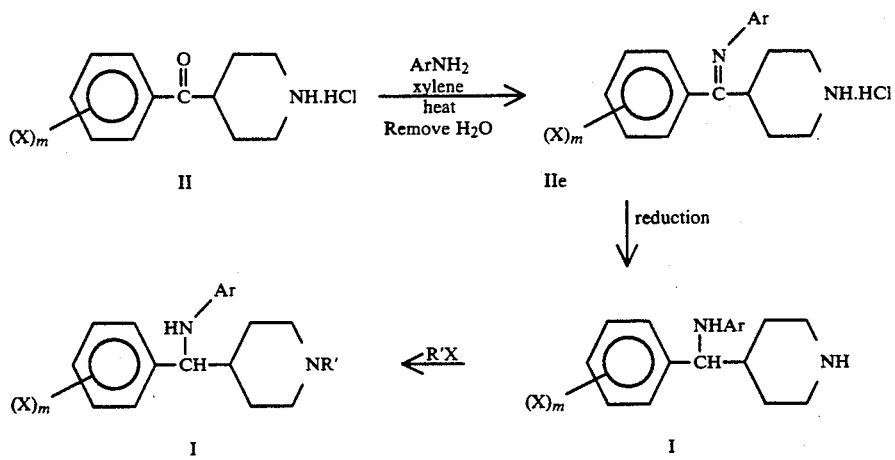

Method C comprises a novel process for preparing compounds of Formula I where R' is H and n is O which avoids the isolation of the intermediate IId. Acid catalysis of the imine formation is provided by employing the hydrogen halide salt, preferably the hydrogen chloride salt, of the intermediate Formula II compound. Water formed in the reaction is removed, preferably by azeotropic distillation. Once the imine is formed, a reducing agent such as lithium aluminum hydride, sodium bis (2-methoxyethoxy) aluminum hydride solution in toluene, sodium borohydride, or sodium cyanoborohydride and the like is introduced into the reaction vessel, along with a solubilizing solvent if needed, accomplishing the reduction of the imine to the Formula I compound (R'=H)) without isolation of the intermediate imine. This provides a Formula I compound to which desired R' groups can be readily attached. Advantageously this method allows fluoroanilines to be used in imine formation without the occurrence of fluorine displacement which can occur if the hydrogen halide salt of the formula II compound is not employed.

Method D

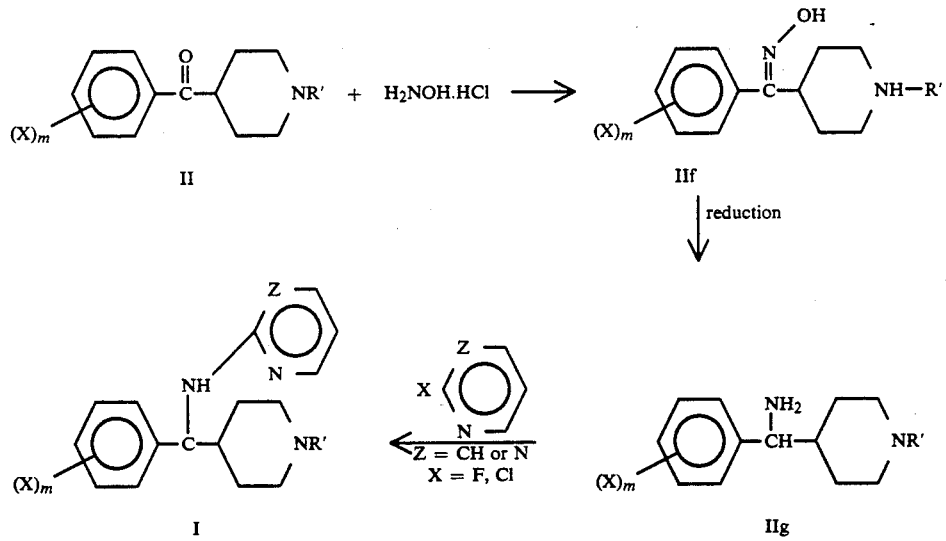

Method D provides an alternative procedure that can be used when sufficiently activated arylhalides are available. The oxime is prepared and reduced, preferably with hydrogen and Raney nickel, using standard laboratory procedures. The aromatic substitution reaction would be carried out under standard conditions to obtain the Formula I compound.

Method E

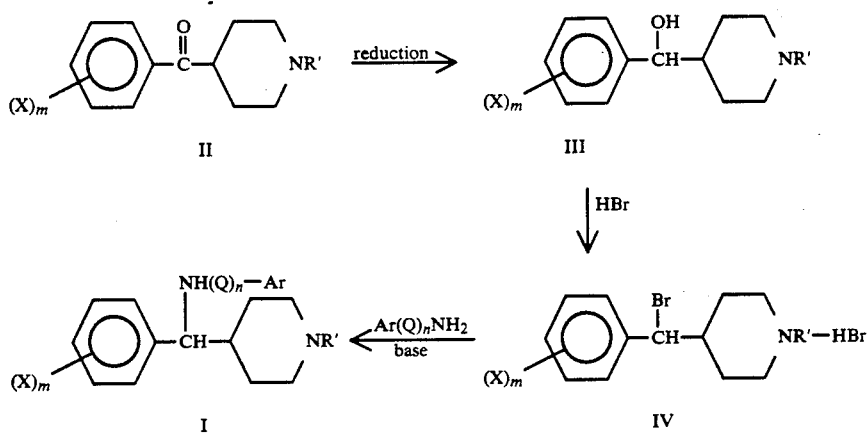

The benzoylazacycloalkanes II are reduced using known chemical procedures to the intermediate alcohol III. Bubbling gaseous hydrogen bromide through a solution of III gives the bromide compound IV which can be reacted with the appropriate amine to obtain a Formula I compound.

Method F

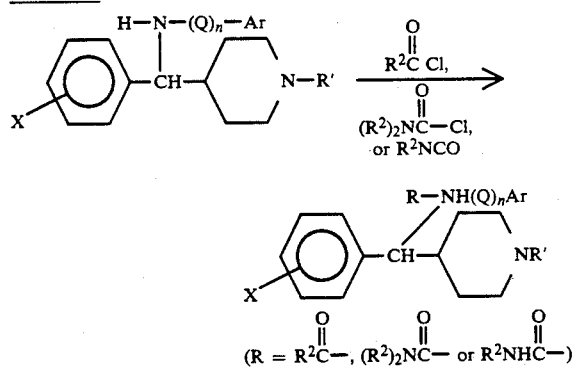

Ureas and amides of Formula I compounds where $R^2$ is as defined previously can be prepared from the appropriate acid halide, carbamoyl chloride or isocyanate by techniques known to those skilled in the art. It would be obvious to one skilled in the art to reduce an amide prepared by this method to the corresponding alkyl or arylalkyl Formula I compound. Furthermore the R group can be lower alkyl and synthesized by alkylation with a loweralkylhalide or sulfate where the R' group would not interfere with the reaction.

The intermediate benzoylazacycloalkanes of Formula II are prepared by known procedures illustrated in the following schemes where the azacycloalkyl group W is represented by the 4-piperidinyl group. The group W also includes 2- and 3-azetidinyl, 2- and 3-pyrrolidinyl, and 2- and 3-piperidinyl.

Scheme I

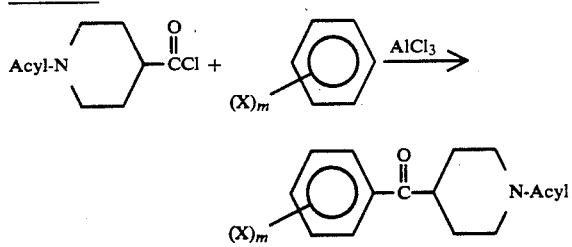

R' is a removable protecting group such as benzyl or a non-interfering group under the definition of R'. M represents the Grignard reagent or the lithium compound which reacts with the nitrile to form an intermediate imine which gives the intermediate of Formula II upon hydrolysis. The reactions are carried out in anhydrous ether or tetrahydrofuran using conventional laboratory techniques.

Scheme II

N-Acylazacycloalkylcarbonyl chlorides and substituted benzenes are reacted together under conventional Freidel-Crafts reaction conditions. The acyl group such as acetyl, benzoyl, carbobenzyloxy, carboethoxy and the like, can be readily removed using standard laboratory procedures to obtain the unsubstituted benzoylazacycloalkanes which provides the intermediates to Formula I compounds. Synthesis of Formula II compounds by Scheme II is discussed in J. Med. Chem. 13, 1-6 (1970) and elsewhere.

Scheme III

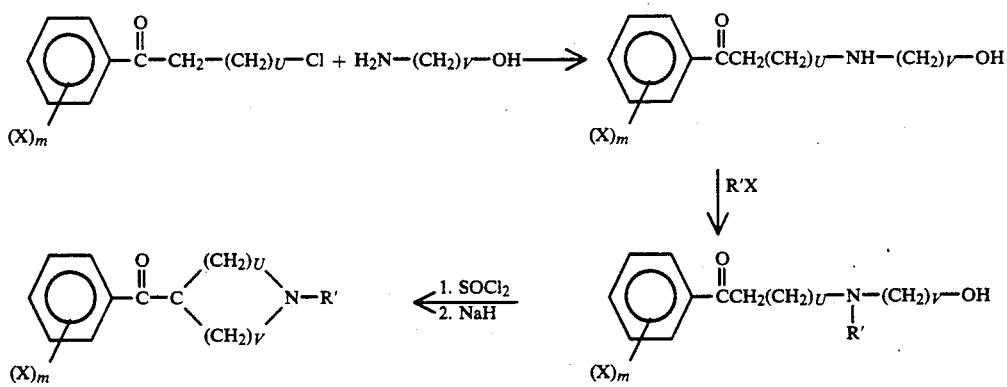

U is 1-2, V is 2-3, U +V ≧ 3

Synthesis by Scheme III is discussed in J. Med. Chem. 13,1-6 (1970).

Other synthetic methods by which Formula II intermediates can be prepared are known in the literature and should be apparent to one skilled in the art.

The foregoing methods of preparation of compounds of Formula I and Formula II are broadly described and the reactions may not be applicable as described to each compound included within the scope of this invention. Where this occurs will be easily recognized by those skilled in the art and such reactions can be carried out by modifications known to those skilled in the art. Exact conditions may vary with substrates, solvents, reagents, temperature, and the like.

Without further elaboration, it is believed that one skilled in the art will be able to carry out this invention without undue experimentation. The following preferred specific embodiments are therefore to be construed as illustrative and not limiting to this disclosure in any way.

The various reagents used in the following preparations and examples are either commercially available or readily synthesized by procedures given in the chemical and patent literature.

PREPARATION 1

4-(p-Fluorobenzoil)-piperidine hydrochloride

A solution of 70.6 g (0.27 mole) of 1-acetyl-4-(p-fluorobenzoyl)piperidine (U.S. Pat. No. 3,576,810, J. Med. Chem. 13(1), 1–5, 1970) in 200 mL of 6N HCl was refluxed for 2 hours. The cooled solution was extracted twice with ether. The aqueous solution was made basic and extracted with benzene. The benzene extracts were dried over anhydrous sodium sulfate and concentrated. The oily residue weighed 38.5 g (69%). The hydrochloride salt was made in the usual manner. Recrystallization of the hydrochloride from isopropanol gave a crystalline solid melting at 222°–224° C.

Analysis calculated for: $C_{12}H_{15}ClFNO$: C, 59.14; H, 6.20; N, 5.75. Found: C, 59.40; H, 6.20; N, 5.73.

PREPARATION 2

(4-Fluorophenyl)[1-(phenylsulfonyl)-4-piperidinyl]methanone

A mixture of 4-(4-fluorobenzoyl)piperidine hydrochloride (53.30 g, 0.219 mol) and benzenesulfonyl chloride (44 g, 0.25 mol) in 500 mL of pyridine was stirred at room temperature overnight. The solvent was removed in vacuo, and the residue was partitioned between $CH_2Cl_2$ and dilute NaOH. The $CH_2Cl_2$ solution was extracted with dilute $H_2SO_4$ and then dried ($MgSO_4$). The volume was reduced to 400 mL, hexane was added, and 39.20 g (50.6%) of the title compound was collected as a white crystalline solid, mp 156.5°–158° C.

Analysis calculated for: $C_{18}H_{18}NO_3SF$: C, 62.23; H, 5.22; N, 4.03. Found: C, 62.13; H, 5.20; N, 4.13.

PREPARATION 3

α-(4-Fluorophenyl)-N-(2-phenylethyl)-1-(phenylsulfonyl)-4-piperidinemethanimine

A mixture of 15.56 g (0.045 mol) of N-benzenesulfonyl-4-(p-fluorobenzoyl)-piperidine, 8.50 g (0.0702 mol) of phenethylamine and 0.20 g (0.0013 mol) of benzenesulfonic acid in 400 mL of toluene was heated at reflux for 111 hr. Water was removed from the reaction mixture with a Dean-Stark trap. The solvent was removed in vacuo, and the residue was partitioned between $CH_2Cl_2$ and dilute $Na_2CO_3$. The $CH_2Cl_2$ solution was dried ($MgSO_4$), and the solvent was removed in vacuo. The residue was recrystallized from ether to give 18.32 g (90.5%) of title compound as a light tan solid, mp 123°–126° C.

Analysis calculated for: $C_{26}H_{27}N_2O_2SF$: C, 69.31; H, 6.04; N, 6.22. Found: C, 68.97; H, 6.04; N, 6.17.

PREPARATION 4

α-(4-Fluorophenyl)-N-(2-phenylethyl)-1-(phenylsulfonyl)-4-piperidinemethanamine

A mixture of 10.0 g (0.022 mol) of α-(4-fluorophenyl)-N-(2-phenylethyl)-1-(phenylsulfonyl)-4-piperidinemethanimine and 1.0 g (0.025 mol) of $LiAlH_4$ in 200 mL of dry THF was stirred at room temperature for 8.5 hr. A 10 mL solution of 10% NaOH was slowly added followed by 100 mL of water. The mixture was extracted with $CH_2Cl_2$, and the solution was dried ($MgSO_4$). The solvent was removed in vacuo to give an oil. This was crystallized from 200 ml of methanol to give 7.32 g (72.9%) of a white crystalline solid, mp 115°–117° C.

Analysis calculated for: $C_{26}H_{29}N_2O_2SF$: C, 69.00; H, 6.46; N, 6.17. Found: C, 69.18; H, 6.45; N, 6.23.

PREPARATION 5

N,α-bis(4-fluorophenyl)-1-(phenylsulfonyl)-4-piperidinemethanimine

A mixture of 13.0 g (0.037 mol) of (4-fluorophenyl)[1-(phenylsulfonyl)-4-piperidinyl]methanone, 24.4 g (0.22 mol) of 4-fluoroaniline, and 0.7 g (0.004 mol) of benzenesulfonic acid in 500 mL of xylene was heated at reflux for 7 days. Water was removed with a Dean-Stark trap. The solvent was removed in vacuo, and the residue was partitioned between $CH_2Cl_2$ and dilute NaOH. The $CH_2Cl_2$ phase was dried ($Na_2SO_4$), and the solvent was removed in vacuo. The residue was recrystallized from $CH_2Cl_2$/hexane to give 11.24 g (69%) of a light grey solid, mp 123°–124° C.

Analysis calculated for: $C_{24}H_{22}N_2SO_2F_2$: C, 65.44; H, 5.03; N, 6.36. Found: C, 65.15; H, 4.97; N, 6.31.

PREPARATION 6

N,α-Bis(4-fluorophenyl)-1-(phenylsulfonyl)-4-piperidine-methanamine

A mixture of 9.20 g (0.021 mol) of N-α-bis(4-fluorophenyl)-1-(phenylsulfonyl)-4-piperidinethanimine and 2.70 g (0.071 mol) of $LiAlH_4$ in 250 mL of dry THF (distilled from sodium/benzophenone ketyl) and under an atmosphere of nitrogen was stirred at room temperature for 17 h. The reaction was quenched with 10% NaOH. Water and $CH_2Cl_2$ were added, and the mixture was filtered through Celite®. The phases were separated, and the organic phases was extracted with water and was dried ($Na_2SO_4$). The solvent was removed in vacuo, and the residue was subjected to flash chromatography (silica gel, elution with $CH_2Cl_2$) to give a solid. This was recrystallized from $CH_2Cl_2$/hexane to give 5.77 g (62.3%) of white solid, mp 175°–176° C.

Analysis calculated for: $C_{24}H_{24}N_2O_2SF_2$: C, 65.14; H, 5.47; N, 6.33. Found: C, 65.04; H, 5.47; N, 6.30.

PREPARATION 7

α-(4-Fluorophenyl)-N-[(4-fluorophenyl)methyl]-1-(phenylsulfonyl)-4-piperidinemethanimine A solution of 22.26 g (0.064 mol) of (4-fluorophenyl)[1-(phenylsulfonyl)-4-piperidinyl]methanone, 12.51 g (0.10 mol) of 4-fluorobenzylamine, and 0.76 g (0.0048 mol) of benzenesulfonic acid in 400 mL of xylene was heated at reflux for 25.5 h. Water was removed with a Dean-Stark trap. The solvent was removed in vacuo, and the residue was partitioned between $CH_2Cl_2$ and dilute NaOH. The $CH_2Cl_2$ solution was dried ($Na_2SO_4$), and the solvent was removed in vacuo. The residue was recrystallized from $CH_2Cl_2$-hexane to give 18.49 g (63.68%) of white crystalline solid, mp 114°–116° C. A second crop of 3.27 g (11.28%) of product was isolated from the filtrate as a white solid, mp 110°–112° C.

Analysis calculated for: $C_{25}H_{24}N_2O_2F_2S$: C, 66.06; H, 5.32; N, 6.16. Found: C, 66.04; H, 5.26; N, 6.14.

PREPARATION 8

α-(4-Fluorophenyl)-N-[(4-fluorophenyl)methyl]-1-(phenylsulfonyl)-4-piperidinemethanamine (E)-2-butenedioate (1:1)

A mixture of 17.0 g (0.037 mol) of α-(4-fluorophenyl)-N-[(4-fluorophenyl)methyl]-1-(phenylsulfonyl)-4-piperidinemethanimine and 1.60 g (0.042 mol) of $LiAlH_4$ in 200 mL of dry THF (distilled from sodium-benzophenone ketyl) and under an atmosphere of nitrogen was stirred at room temperature for 23 h. The reaction was quenched with 10% NaOH. $CH_2Cl_2$ was added, and the mixture was filtered through Celite. The filtrate was extracted with water and was dried ($Na_2SO_4$). The resulting oil was purified with flash chromatography (silica gel, eluted with $CH_2Cl_2$ and 1% $CH_3OH$ in $CH_2Cl_2$) to give an oil. This was converted to the fumarate salt, and the salt was recrystallized from $CH_3OH$/ether to give 14.37 g (67.8%) of white solid, mp 213°–214° C.

Analysis calculated for: $C_{29}H_{30}N_2O_6F_2S$: C, 60.83; H, 5.28; N, 4.89. Found: C, 60.81; H, 5.26; N, 4.92.

PREPARATION 9

4-(p-Fluorobenzoyl)-1-(3-phenoxypropyl)piperidine hydrochloride hemihydrate

A mixture of 12.2 g (0.05 mole) of 4-(p-fluorobenzoyl)piperidine hydrochloride, 11.8 g (0.055 mole) of 3-phenoxypropyl bromide and 30.4 g (0.022 mole) of anhydrous potassium carbonate in 150 mL of 1-butanol was refluxed for 20 hours. The mixture was filtered, and the filtrate was concentrated. The solid residue which remained was dissolved in isopropanol and an excess of ethereal HCl was added. The hydrochloride salt crystallized upon cooling of the solution. Recrystallization from 2-propanol gave 10.9 g (58%) of the hydrochloride salt which melted at 196°–198° C.

Analysis calculated for: $C_{42}H_{52}N_2Cl_2F_2O_5$: C, 65.19; H, 6.51; N, 3.62. Found: C, 65.57; H, 6.68, N, 3.67.

PREPARATION 10

(4-Fluorophenyl)[1-(3-phenoxypropyl)-4-piperidinyl]methanone oxime

A solution of the HCl salt of 4-(p-fluorobenzoyl)-1-(3-phenoxypropyl)piperidine (7.54 g, 0.02 mol) and hydroxylamine hydrochloride (2.44 g, 0.035 mol) was prepared in 75 mL of 95% ethanol. To this solution was added 10 mL of water to produce a suspension. Next, sodium hydroxide (8.0 g, 0.2 mol) dissolved in 15 mL of water was added dropwise with stirring. The resultant was heated at reflux for an hour, and two separate phases resulted. The suspension was diluted to 1500 mL with water and extracted with chloroform. The chloroform layer was back extracted with water and 5% sodium hydroxide. The chloroform layer was dried ($Na_2SO_4$) and filtered. When chloroform was removed, a white solid was obtained (6.54 g, 91.9%). A one gram sample was recrystallized from methylene chloride-isopropyl ether. A white solid was isolated and dried in vacuo overnight at 80° C. This process furnished 0.68 g (62.5%) of white crystalline solid, mp 163.5°–166.5° C.

Analysis calculated for: $C_{21}H_{25}N_2O_2F \cdot 0.25H_2O$: C, 69.88; H, 7.12; N, 7.76. Found: C, 69.61; H, 7.00; N, 7.68.

PREPARATION 11

α-(4-Fluorophenyl)-1-(3-phenoxypropyl)-4-piperidinemethanamine dihydrochloride hemihydrate A suspension of the (4-fluorophenyl)[1-(3-phenoxypropyl)-4-piperidinyl]methanone oxime (5.00 g, 0.014 mol) in 100 mL of ethanol was subjected to hydrogenation (52 psi) in the presence of Raney nickel for 16 hours at room temperature. The catalyst was removed by filtration, and ethanol was removed by the rotary evaporator to give a clear oil. This oil was converted to the HCl salt in methanol using ethereal HCl. A white solid was isolated and dried in vacuo 16 hours at 80° C. in the presence of phosphorus pentoxide. This process provided 3.22 g (54.2%) of white crystalline solid, mp 247°-248° C. (dec).

Analysis calculated for: $C_{21}H_{27}FN_2O \cdot 2HCl \cdot 0.5H_2O$: C, 59.43; H, 7.13; N, 6.60. Found: C, 59.47; H, 7.14; N, 6.59.

PREPARATION 12

4-(p-Fluorobenzoyl)-1-phenethylpiperidine hydrochloride

A mixture of 12.2 g (0.05 mole) of 4-(p-fluorobenzoyl)piperidine hydrochloride, 10.2 g (0.055 mole) of phenethyl bromide, and 27.6 g (0.2 mole) of potassium carbonate in 150 mL of 1-butanol was allowed to reflux for 2 hours. The mixture was filtered, and the filtrate concentrated. The solid residue which remained weighed 14.8 g (95%). The hydrochloride salt was prepared in the usual manner and after recrystallization from isopropanol, melted at 254°-257° C.

Analysis calculated for: $C_{20}H_{23}ClFNO$: C, 69.05; H, 6.66; N, 4.03. Found: C, 69.02; H, 6.62; N, 4.03.

PREPARATION 13

2-[(Ethoxycarbonyl)amino]benzoic acid ethyl ester

A mixture of ethyl 2-aminobenzoate (ethyl anthranilate) (50.0 g, 0.30 mole) and ethyl chloroformate (32.8 g, 0.30 mole) in 400 mL of xylenes was heated at reflux for 8 hours. The xylene was removed and the residue was dissolved in chloroform. The chloroform layer was extracted with 5% sodium hydroxide, dried ($Na_2SO_4$), filtered, and the chloroform removed to give an oil which crystallized. The solid was triturated with isopropyl ether and placed in the freezer. Two crops of white solid were obtained and dried in vacuo overnight at room temperature. This provided 67.95 g (97.6% yield) of white crystalline solid, mp 41°-42° C.

Analysis calculated for: $C_{12}H_{15}NO_4$: C, 60.75; H, 6.37; N, 5.90. Found: C, 60.68; H, 6.41; N, 5.92.

PREPARATION 14

3-(2-Hydroxyethyl)-2,4(1H,3H)-quinazolinedione

A mixture of 2-[(ethoxycarbonyl)amino]benzoic acid ethyl ester (65.75 g, 0.277 mol) and 2-aminoethanol (16.9 g, 0.277 mol) was refluxed for 2.5 days in 350 mL of xylenes. The reaction was cooled to room temperature and xylene was removed. Chloroform was added to the residue and a brown solid crystallized. The brown solid was filtered from the solution. The chloroform layer was extracted with water, dried ($Na_2SO_4$), filtered and the solvent was removed. The residue was placed in the freezer in isopropyl alcohol. The brown solid was triturated with isopropyl alcohol. Both produced a crystalline white solid which was dried in vacuo overnight at 80° C. This gave a total of 40.70 g (71.3% yield) of white crystalline solid, mp 250°-252° C.

Analysis calculated for: $C_{10}H_{10}N_2O_3$: C, 58.25; H, 9.89; N, 13.59. Found: C, 58.14; H, 4.84; N, 13.50.

PREPARATION 15

3-(2-Chloroethyl-2,4(1H,3H)-quinazolinedione

A solution of 3-(2-hydroxyethyl)-2,4(1H,3H)-quinazolinedione (16.23 g, 0.079 mole) and thionyl chloride (9.76 g, 0.082 mole) was heated at reflux for 22 hours in 300 mL of chloroform. The solution was concentrated to dryness and a white solid was obtained. The solid was triturated with diethyl ether and placed in the refrigerator freezer. The white solid was filtered and washed with diethyl ether. The solid was dried in vacuo overnight at 80° C. This provided 26.50 g (93.2% yield) of white crystalline solid, mp 189°-192° C.

Analysis calculated for: $C_{10}H_9N_2O_2Cl$: C, 53.47; H, 4.04; N, 12.47. Found: C, 53.24; H, 4.05; N, 12.34.

PREPARATION 16

4-(3-Chloropropoxy)benzoic acid 1,1-dimethylethyl ester

A mixture of 4-hydroxybenzoic acid 1,1-dimethylethyl ester (U.S. Pat. No. 3,625,954) (35.0 g, 0.1804 mol), 3-chlorobromopropane (56.81 g, 0.361 mol), and potassium carbonate (69.1 g, 0.5 mol) was heated 20 h at reflux in 600 mL of acetone. The mixture was cooled to room temperature and filtered. The solvent was removed in vacuo to give an oil. The oil was dissolved in hexanes (400 mL), and the solution was chilled in the freezer. A white solid crystallized and was separated. The solid was dried in vacuo for 6 h at room temperature. This procedure furnished 39.46 g (81%) of a white crystalline solid, mp 57.5°-58.5° C.

Analysis calculated for: $C_{14}H_{19}O_3Cl$: C, 62.11; H, 7.07. Found: C, 62.02; H, 7.24.

PREPARATION 17

(4-Fluorophenyl)[1-(1-methylethyl)-4-piperidinyl]methanone

A mixture of 34.16 g (0.165 mol) of the 4-(4-fluorobenzoyl)piperidine, 33.80 g (0.199 mol) of isopropyl iodide and excessive sodium bicarbonate in 600 mL of acetonitrile was heated at reflux for 14 h. The solvent was removed in vacuo, and the residue was partitioned between $CH_2Cl_2$ and dilute NaOH. The $CH_2Cl_2$ solution was dried ($Na_2SO_4$), and the solvent was removed in vacuo to give a solid. This was recrystallized from $CH_2Cl_2$/hexane to give 31.89 g (77.6%) of crystalline solid, mp 120°-121° C.

Analysis calculated for: $C_{15}H_{20}NOF$: C, 72.26; H, 8.09; N, 5.62. Found: C, 72.21; H, 8.16; N, 5.64.

PREPARATION 18

2-Benzoyl-1-(3-phenoxypropyl)piperidine

Following the procedure of Preparation 9, the title compound is prepared from 2-benzoylpiperidine [U.S. Pat. No. 3,459,750; Helv. Chim. Acta. 38, 134–40 (1955)].

PREPARATION 19

1-(3-Phenoxypropyl)-3-(3-trifluoromethylbenzoyl)pyrroldine

Following the procedure of Preparation 9, the title compound is prepared from 3-(3-trifluoromethylbenzoyl)pyrroldine (U.S. Pat. No. 3,489,769) and 3-phenoxypropyl bromide.

PREPARATION 20

2-Cyano-1-(3-phenoxypropyl)piperidine

Following the procedure of Preparation 9, the title compound is prepared from 3-phenoxypropyl bromide and 2-cyanopiperidine [Chem. Ber. 92, 1608–1613 (1959), Helv. Chim. Acta 46(4), 1190–1206 (1963)].

PREPARATION 21

2-Cyano-1-(3-phenoxypropyl)pyrrolidine

Following the procedure of Preparation 9, the title compound is prepared from 2-cyanopyrrolidine [Helv. Chim. Acta 50(8), 2520–2531 (1967)] and 3-phenoxypropyl bromide.

PREPARATION 22

3-(4-Fluorobenzoyl)azetidine

Following the procedure for the preparation of 1-benzyl-3-benzoylpyrrolidine (U.S. Pat. No. 3,479,370) and using 1-benzhydryl-3-cyanoazetidine [J.O.C. 37(24), 3953–55, (1972)] and 4-fluorophenylmagnesium bromide, 1-benzhydryl-3-(4-fluorobenzoyl)azetidine is obtained. The benzhydryl group is removed by catalytic hydrogenation using palladium on carbon to obtain the title compound.

PREPARATION 23

2-(4-Fluorobenzoyl)azetidine

Following the procedure for the preparation of 1-benzyl-3-benzoyl-pyrrolidine (U.S. Pat. No. 3,479,370) and using 1-benzhydryl-2-cyanoazetidine (G.B. 1,517,934) and 4-fluorophenylmagnesium bromide, 1-benzhydryl-2(4-fluorobenzoyl)azetidine is obtained. The benzhydryl group is removed by catalytic hydrogenation using palladium on carbon to obtain the title compound.

PREPARATION 24

(S)-2-(4-Fluorobenzoyl)pyrrolidine

Using procedures given in J. Chem. Soc. Perkin Trans. I, 1987, 1469, (S)-1-ethoxycarbonylproline is reacted with diphenylphosphinoyl chloride in the presence of triethylamine to form the mixed anhydride. The mixed anhydride is treated with 4-fluorophenylmagnesium bromide to obtain (S)-1-ethoxycarbonyl-2-(4-fluorobenzoyl)pyrrolidine. Hydrolysis with methanotic potassium hydroxide gives the title compound.

PREPARATION 25

2-(4-Fluorobenzoyl)-1-(3-phenoxypropyl)pyrrolidine

Following the procedure for the preparation of 1-benzyl-3-benzoylpyrrolidine (U.S. Pat. No. 3,479,370) the title compound is prepared from 2-cyano-1-(3-phenoxypropyl)pyrrolidine and 4-fluorophenylmagnesium bromide.

PREPARATION 26

2(4-Fluorobenzoyl)-1-(3-phenoxypropyl)piperidine

Following the same procedure as Preparation 25, the title compound is prepared from 2-cyano-1-(3-phenoxypropyl)piperidine and 4-fluorophenylmagnesium bromide.

PREPARATION 27

3-(4-Fluorobenzoyl)-1-(2-naphthalenylmethyl)azetidine

Following the procedure of Preparation 9, the title compound is prepared from 2-bromomethylnaphthalene and 3-(4-fluorobenzoyl)azetidine.

PREPARATION 28

2-(4-Fluorobenzoyl)-1-(3-phenoxypropyl)azetidine

Following the procedure of Preparation 9, the title compound is obtained from 2-(4-fluorobenzoyl)azetidine and 3-phenoxypropyl bromide.

PREPARATION 29

α,β-(Benzoyloxy)-4-[(4-fluorophenyl)[(4-fluorophenyl)amino]methyl]-oxo-1-piperidinebutanoic acid hemihydrate A solution of N,α-bis(4-fluorophenyl)-4-piperidinemethanamine (5.0 g, 0.017 mol) in 50 mL of warm dioxane (previously dried over basic alumina) was added to a solution of dibenzoyl-L-tartaric anhydride (5.78 g, 0.017 mol) in dried dioxane (50 mL). The reaction was heated to 70° C. for 2 h. At that time TLC analysis (EtOAc:MeOH:NH$_4$OH, 7:2:1) indicated the reaction was complete. The dioxane was evaporated thoroughly and the crystalline residue dissolved in hot isopropyl alcohol (30 mL) and allowed to cool. The crystals which precipitated upon cooling were collected and recrystallized again from hot isopropyl alcohol (25 mL). After cooling the solid was collected and dried to obtain 1.24 g (11.4% yield), mp 147°–150° C., [α]$_D$= −61.6 (C=1, MeOH).

Analysis calc'd for: $C_{36}H_{32}N_2O_7F_2 \cdot 0.5H_2O$: C, 66.35; H, 5.10; N, 4.30. Found: C, 66.24; H, 4.94; N, 4.24.

PREPARATION 30

(+)-α,β-Bis(benzoyloxy)-4-[(4-fluorophenyl)[(4-fluorophenyl)[(4-fluorophenyl)amino]methyl]-gamma-oxo-1-piperidinebutanoic acid hemihydrate A solution of N,α-bis(4-fluorophenyl)-4-piperidinemethanamine (8.33 g, 0.028 mol) in warm dry dioxane (50 mL) was combined with a solution of dibenzoyl-D-tartaric anhydride (9.38 g, 0.028 mol) in dioxane (50 mL). The reaction stirred at room temperature overnight. At that time TLC analysis (EtOAe:MeOH:NH$_4$OH 7:2:1) indicated the reaction was complete. The solvent was evaporated thoroughly and the crystalline residue was dissolved in hot isopropyl alcohol (180 mL) and allowed to cool slowly. Crystals precipitated upon cooling and were collected and dried then recrystallized again from isopropyl alcohol (50 mL). The crystals obtained after cooling were collected, rinsed with cold isopropyl alcohol and dried (3.0 g, 16.7%), mp 147°–150° C., [α]$_D^{22}$= +61.5 (C=1, MeOH).

Analysis calc'd for: $C_{36}H_{32}N_2O_7F_2 \cdot 0.5H_2O$: C, 66.35; H, 5.10; N, 4.30. Found: C, 66.49; H, 4.90; N, 4.33.

PREPARATION 31

(4-Fluorophenyl)[1-(2-naphthalenylmethyl)-4-piperidinyl]methanone

A mixture of 15.1 g (0.062 mol) 4-(4-fluorobenzoyl)-piperidine hydrochloride, 13.77 g (0.062 mol) of 2-(bromomethyl)naphthalene and 13.6 g (0.16 mol) of sodium bicarbonate in 500 mL of absolute ethanol was stirred at room temperature for 16 hr. The solvent was partitioned between CH$_2$Cl$_2$ and dilute NaOH. The CH$_2$Cl$_2$ solution was dried (Na$_2$SO$_4$), and the solvent was removed in vacuo. The residue was recrystallized from 400 mL of methanol to give 11.81 g (54.9%) of white crystalline solid, mp 131°–134° C. The filtrate was subjected to flash chromatography (silica gel, gradiently eluted with CH₃OH/CH₂Cl₂) to give an additional 2.84 g (13.2%) of the title compound.

Analysis calculated for: $C_{23}H_{22}NOF$: C, 79.51; H, 6.38; N, 4.03. Found: C, 79.50; H, 6.38; N, 4.08.

PREPARATION 32

Following the procedure of Preparation 31 using 2-(bromomethyl)naphthalene and
a. 4-benzoylpiperidine
b. 4-(4-trifluoromethylbenzoyl)piperidine
c. 4-(4-methoxybenzoyl)piperidine
there are obtained respectively:
a. 4-benzoyl-1-(2-naphthalenylmethyl)piperidine
b. 1-(2-naphthalenylmethyl)-4-(4-trifluoromethylbenzoyl)piperidine
c. 4-(4-methoxybenzoyl)-1-(2-naphthalenylmethyl)piperidine.

PREPARATION 33

1-Chloro-4-[(3-chloropropyl)sulfinyl]benzene

To a stirred solution of 206.76 g (0.44 mol) of 1-chloro-4-[(3-chloropropyl)thio]benzene (J.A.C.S. 82, 2505, 1960) and 111.50 g of 30% H₂O₂ (0.98 mol) in 1 L of acetone chilled in a dry ice acetone bath was added 90 mL of concentrated sulfuric acid. The ice bath was removed and the mixture stirred at ambient temperature for 16 hr. The mixture was diluted with 1 L of water and extracted with two 500 mL portions of CH₂Cl₂. The extracts were dried (MgSO₄) and concentrated separately and the residual material from both extractions shown to be a mixture of product and starting material. The impure product was chromatographed on Florisil (4×75 cm) using petroleum ether-chloroform for elution. The yield was 50.36 g.

PREPARATION 34

1-Chloro-4-[(3-chloropropyl)sulfonyl]benzene

To a stirred solution of 58.50 g (0.266 mol) of 1-chloro-4-[(3-chloropropyl)thio]benzene in 125 mL of glacial acetic acid cooled in an ice bath was added 69 g of 30% H₂O₂ (0.609 mol). The mixture was stirred for 0.5 hr at ice bath temperature and then stirred at ambient temperature for 24 hr. The mixture was then heated at 80° C. for 20 hr. The reaction mixture was generated by addition of water (300 mL) and chloroform (300 mL). The mixture was stirred for 10 minutes and the phases separated. The organic layer was washed with an aqueous solution of sodium sulfite and then with aqueous 1M NaOH solution. The organic solution was dried (MgSO₄) and concentrated to give a white solid. The solid was recrystallized from chloroform-ether at freezer temperature to obtain 57.74 g (86%), mp 72.5–73.5. The filtrate was concentrated to an oil which was triturated with ether and chilled in a freezer to obtain a second crop of 4.53 g (6.8%), mp 69°–72° C. The total yield was 62.27 g (92.8%).

PREPARATION 35

4-(3,4-Difluorobenzoyl)piperidine

Following the procedure for the preparation of 1-acetyl-4(4-fluorobenzoyl)piperidine (U.S. Pat. No. 3,576,810), 1-acetyl-4(3,4-difluorobenzoyl)piperidine is prepared from 1-acetylisonipecotic acid chloride and 1,2-difluorobenzene. The acetyl group is removed by hydrolysis in dilute hydrochloric acid. Basification followed by extraction with a suitable solvent yields the title compound.

PREPARATION 36

4-(4-Trifluoromethylbenzoyl)piperidine

The title compound is prepared from 1-acetyl-4-cyanopiperidine and 4-trifluoromethylphenylmagnesium bromide according to the procedure given for 4-(3-trifluoromethylbenzoyl)piperidine in J. Med. Chem. 13, 1–6 (1970).

PREPARATION 37

4-(3,4-Difluorobenzoyl)-1-(2-naphthalenylmethyl)-piperidine

Following the procedure of Example 31, the title compound is obtained from 4-(3,4-difluorobenzoyl)-piperidine and 2-bromomethylnaphthalene.

PREPARATION 38

2-(4-Fluorobenzoyl)-1-(3-phenoxypropyl)pyrrolidine

2-Cyano-1-(3-phenoxypropyl)pyrrolidine is reacted with 4-fluorophenylmagnesium bromide according to the usual procedures to obtain the title compound.

PREPARATION 39

2-(4-Fluorobenzoyl)-1-(3-phenoxypropyl)piperidine

The title compound is obtained from a reaction of 4-fluorophenylmagnesium bromide with 2-cyano-1-(3-phenoxypropyl)piperidine.

PREPARATION 40

(3,4-Dichlorophenyl)(1-acetylpiperidin-4-yl)methanone

To a slurry of 53.2 g (0.4 mol) of aluminum chloride in 80 mL of diclorobenzene was added portionwise 38.0 g (0.2 mol) of N-acetylisonipecotic acid chloride (by closed addition method) so as to maintain at 5°–10°. During the addition a total of 50 mL of methylene chloride was added as needed. After the addition was complete the mixture was allowed to come to room temperature and stirred for two days. The mixture was poured onto an excess of crushed ice. The aqueous mixture was extracted several times with chloroform. The collected extracts were dried over anhydrous sodium sulfate and the mixture was filtered. The filtrate was concentrated under reduced pressure and the residue was triturated in isopropyl ether. The residue crystallized and 22 g (36.5%) of crude product was obtained. A 5-g sample was recrystallized from acetone-water after treatment with charcoal. After air-drying the off-white solid was recrystallized from isopropyl ether-methanol, mp 134°–136°.

Analysis calculated for: $C_{14}H_{15}Cl_2NO_2$: C, 56.01; H, 5.04; N, 4.67. Found: C, 55.83; H, 5.03; N, 4.62.

PREPARATION 41

(3,4-Dichlorophenyl)(4-piperidinyl)methanone hydrochloride hemihydrate

A slurry of 15 g (0.05 mol) of 1-acetyl-4-(3,4-dichlorobenzoyl)piperidine in 150 mL of 6N hydrochloric acid was heated at mild reflux for 23 hr. The mixture was cooled and neutralized using 50% sodium hydroxide solution and ice. The mixture was extracted several times with benzene and the collected extracts were dried over anhydrous sodium sulfate. The mixture was filtered and the filtrate was concentrated under reduced pressure. The residue obtained weighed 11.1 g (86%). The hydrochloride salt was made in the usual manner on 5 g of the free base. Recrystallization from isopropyl alcohol-ether gave a crystalline solid, mp 221-223.

Analysis calculated for: $C_{24}H_{30}Cl_6N_2O_3$: C, 47.62; H, 5.00; N, 4.62. Found: C, 47.46; H, 4.86; N, 4.58.

PREPARATION 42

2-(3-Chloropropyloxy)naphthalene

A mixture of 2-naphthol (72.07 g, 0.5 mol), 1-chloro-3-bromopropane (78.72 g, 0.5 mol), and potassium carbonate (103.65 g, 0.75 mol) was heated at reflux 16 hr in 750 mL of acetone. The mixture was cooled to room temperature and filtered. The reaction was concentrated to a viscous oil using a rotary evaporator. The oil was dissolved in chloroform and washed with 5% sodium hydroxide and water. The chloroform was dried ($Na_2SO_4$) and filtered. Chloroform was removed to give a brown solid. A ten-gram sample was subjected to flash chromatography on silica gel using 2% ethyl acetate-hexanes, 3% ethylacetate-hexanes, 5% ethyl acetate-hexanes, and 10% ethyl acetate-hexanes for elution. Fractions of similar purity were combined and solvents removed. A clear oil was obtained and dried 16 hr at 80° C. A white crystalline solid was formed on standing at room temperature. This procedure provided 7.01 g (52.2%) of white crystalline solid, mp 46°-49° C.

Analysis calculated for: $C_{13}H_{13}OCl$: C, 70.75; H, 5.74. Found: C, 70.79; H, 5.89.

PREPARATION 43

3-(4-Fluorobenzoyl)pyrrolidine

1-Benzyl-3-(4-fluorobenzoyl)pyrrolidine is prepared by reacting 1-benzyl-3-cyanopyrrolidine with 4-fluorophenylmagnesium bromide by well known procedures. Removal of the benzyl group by catalytic debenzylation gives the title compound.

PREPARATION 44

3-(4-Fluorobenzoyl)piperidine

Reaction of 1-acetylnipecotoyl chloride with fluorobenzene by the procedures used to prepare the compound of Preparation 1 gives the title compound.

PREPARATION 45

α-(4-Fluorophenyl)-N-(phenylmethyl)-1-(phenylsulfonyl)-4-piperidinemethanimine A mixture of 10.32 g (0.0297 mol) of N-benzenesulfonyl-4-(p-fluorobenzoyl)piperidine, 5.4 g (0.0505 mol) of benzylamine and 0.5 g (0.0032 mol) of benzenesulfonic acid in 500 mL of toluene was heated at reflux. Water was removed from the reaction mixture with a Dean-Stark trap. After 134.5 h, the solvent was removed in vacuo, and the residue was partitioned between $CH_2Cl_2$ and dilute NaOH. The $CH_2Cl_2$ solution was dried ($MgSO_4$), the volume was reduced to 100 mL, and 200 mL of ether was added. A precipitate was collected to give 10.0 g (77.1%) of the title compound as a white crystalline solid, mp 153°-155°C.

Analysis calculated for: $C_{25}H_{25}N_2SO_2F$: C, 68.78; H, 5.77; N, 6.42. Found: C, 68.63; H, 5.76; N, 6.39.

EXAMPLE 1

N,α-Bis(4-fluorophenyl)-4-piperidinemethanamine (E)-2-butendioate (1:1) hemihydrate A mixture of 31.6 g (0.072 mol) of N,α-bis(4-fluorophenyl)-1-(phenylsulfonyl)-4-piperidinemethanamine and 32 g (0.34 mol) of phenol in 200 mL 48% HBr was heated at reflux for 2 hr and then was poured over ice. The mixture was made basic with 50% NaOH, and the basic mixture was extracted with $CH_2Cl_2$. The $CH_2Cl_2$ solution was dried ($Na_2SO_4$), and the solvent was removed in vacuo to give a gum. This was subjected to flash chromatography (silica gel, eluted with 5% $NH_4OH$ in $CH_3OH$) to give 6.81 g (28.7%) of the desired product as the nonsalt form. This was converted to the fumarate salt, and the salt was recrystallized from methanol/ether to give 5.59 g (18%) of the title compound as a white crystalline solid, mp 136°-141° C.

Analysis calculated for: $C_{22}H_{25}N_2F_2O_{4.5}$: C, 61.82; H, 5.90; N, 6.55. Found: C, 62.13; H, 5.72; N, 6.48.

EXAMPLE 2

1-[4-[3-[4-[(4-Fluorophenyl)[4-fluorophenyl)amino]methyl]-1-piperidinyl]propoxy]-3-methoxyphenyl]ethanone hemihydrate A mixture of 3.22 g (10.8 mmol) of N,α-bis(4-fluorophenyl)-4-piperidinemethanamine, 2.90 g (12.0 mmol) of 3-chloro-1-(4-acetyl-2-methoxyphenoxy) propane, and 2.90 g (35 mmol) of sodium bicarbonate in 400 mL of 1-butanol was heated at reflux for 17.5 h. The solvent was removed in vacuo, and the residue was partitioned between $CH_2Cl_2$ and diluted NaOH. The $CH_2Cl_2$ solution was dried ($Na_2SO_4$), and the solvent was removed in vacuo to give an oil. This was subjected to flash chromatography by (silica gel, eluted gradiently with 1% to 5% $CH_3OH$ in $CH_2Cl_2$) to give 3.53 g (63.1%) of the title compound as a noncrystalline solid.

Analysis calculated for: $C_{30}H_{35}N_2O_{3.5}$: C, 69.61; H, 6.82; N, 5.41. Found: C, 69.88; H, 6.67; N, 5.43.

EXAMPLE 3

4-[(4-Fluorophenyl)[(4-fluorophenyl)amino]methyl]-1,1-bis(3-phenyl-2-propenyl)piperidinium chloride A mixture of 34.41 g (11.3 mmol) of N-α-bis(4-fluorophenyl)-4-piperidinemethanamine, 1.85 g (12.1 mmol) of cinnamyl chloride and 2.00 g (19 mmol) of sodium carbonate in 300 mL of acetonitrile was stirred at room temp overnight. The solvent was removed in vacuo, and the residue was partitioned between $CH_2Cl_2$ and dilute NaOH. The residue was recrystallized from $CH_2Cl_2$/hexane to give 1.25 g (19.4%) of a white crystalline solid, mp 215°-216° C.

Analysis calculated for: $C_{36}H_{37}N_2F_2Cl$: C, 75.71; H, 6.53; N, 4.91. Found: C, 75.07; H, 6.48; N, 4.85.

EXAMPLE 4

N,α-Bis(4-fluorophenyl)-1-(1-methylethyl)-4-piperidinemethanamine dihydrochloride monohydrate A mixture of 29.36 g (0.103 mol) of (4-fluorophenyl)[1-(1-methylethyl)-4-piperidinyl]methanone hydrochloride, 28.9 g (0.260 mol) of 4-fluoroaniline and 0.61 g (3.9 mmol) of benzenesulfonic acid in 500 mL of xylene was heated at reflux for 20 h. Water was removed with a Dean-Stark trap. The solvent was removed in vacuo. The residue was reacted with 6.0 g (0.16 mol) of $LiAlH_4$ in 400 mL of THF at room temperature. After 23 h, dilute NaOH and then water were added slowly. The mixture was filtered through Celite ®, and CH₂Cl₂ (400 mL) was added to the filtrate. The mixture was extracted with several portions of water and was dried (Na₂SO₄). The solvent was removed in vacuo. The residue was dissolved in CH₃OH and treated with an excess of ethereal HCl. The hydrochloride salt was collected to give 13.8 g (32.1%) of the title compound as a white solid, mp 225°–228° C. An additional 4.58 g (10.2%) of product was collected from the filtrate.

Analysis calculated for: $C_{21}H_{30}N_2F_2Cl_2O$: C, 57.93; H, 6.95; N, 6.43. Found: C, 57.96; H, 6.91; N, 6.41.

EXAMPLE 5

N,α-bis(4-fluorophenyl)-1-(3-phenyl-2-propenyl)-4-piperidinemethanamine dihydrochloride hemihydrate A mixture of 3.41 g (11.3 mmol) of the N,α-bis(4-fluorophenyl)-4-piperidinemethanamine, 1.85 g (12.1 mmol) of cinnamyl chloride, and 2.00 g (19.0 mmol) of sodium carbonate in 300 mL of acetonitrile was stirred at room temperature overnight. The solvent was removed in vacuo, and the residue was partitioned between CH₂Cl₂ and dilute NaOH. An insoluble residue was removed by filtration. The CH₂Cl₂ solution was subjected to flash chromatography (silica gel, eluted with 3% CH₃OH in CH₂Cl₂) to give an oil. This was converted to the HCl salt, and the salt was recrystallized from CH₃OH/ether to give 1.83 g (32.7%) as a white crystalline solid, mp 239°–241° C.

Analysis calculated for: $C_{27}H_{31}N_2F_2Cl_2O_{0.5}$: C, 65.80; H, 6.24; N, 5.60. Found: C, 65.14; H, 6.13; N, 5.68.

EXAMPLE 6

4-[(4-Fluorophenyl)[(4-fluorophenyl)amino]methyl]-α-(phenoxymethyl)-1-piperidineethanol dihydrochloride hemihydrate A mixture of 3.41 g (11.3 mmol) of the N,α-bis(4-fluorophenyl)-4-piperidinemethanamine and 2.20 g (14.7 mmol) of 1,2-epoxy-3-phenoxypropane in 400 mL of acetonitrile was heated at reflux for 46 h. The solvent was removed in vacuo, and the residue was subjected to flash chromatography (silica gel, eluted with 3% CH₃OH in CH₂Cl₂) to give an oil. This was converted to the HCl salt, and the salt was recrystallized from CH₃OH-ether to give give 3.20 g (53%) of a crystalline white solid, mp 229°–232° C.

Analysis calculated for: $C_{27}H_{30}N_2O_2 \cdot 2HCl \cdot 0.5H_2O$: C, 0.68; H, 6.22; N, 5.24. Found: C, 60.49; H, 6.15; N, 5.20.

EXAMPLE 7

4-[(4-Fluorophenyl)[(4-fluorophenyl)amino]methyl]-α-(phenoxymethyl)-1-piperidineethanol dihydrochloride hemihydrate In the preparation of the compound of Example 6, an additional crop of material was obtained from the mother liquers to give 0.53 g (8.8%) of white crystalline solid which was shown by ¹³C NMR to be a diastereomer of the compound of Example 6, mp 212°–216° C.

Analysis calculated for: $C_{27}H_{30}N_2O \cdot 2HCl \cdot 0.5H_2O$: C, 60.68; H, 6.22; N, 5.24. Found: C, 60.49; H, 6.15; N, 5.20.

EXAMPLE 8

N,α-bis(4-Fluorophenyl)-1-(3-phenoxypropyl)-4-piperidinemethanamine dihydrochloride hemihydrate A mixture of 3.92 g (10.5 mmol) of N,α-bis(4-fluorophenyl)-4-piperidinemethanamine hydrochloride hydrate, 2.77 g (13.0 mmol) of 3-phenoxy propyl bromide, 3.80 g (36.0 mmol) of sodium carbonate, and 0.61 g (3.7 mmol) of KI in 400 mL of 1-butanol was heated at reflux for 69 h. The solvent was removed in vacuo, and the residue was partitioned between CH₂Cl₂ and dilute NaOH. The CH₂Cl₂ solution was dried (Na₂SO₄), and the solvent was removed in vacuo. The residue was subjected to flash column chromatography (silica gel, elution with 1 to 3% CH₃OH in CH₂Cl₂) to give the free base of the title compound. This was converted to the HCl salt, and the salt was recrystallized from CH₃OH/ether to give 3.59 g (65.9%) of the title compound as a white crystalline solid, mp 222°–226° C.

Analysis calculated for: $C_{27}H_{33}N_2O_{1.5}F_2Cl_2$: C, 62.55; H, 6.42; N, 5.40. Found: C, 62.18; H, 6.26; N, 5.39.

EXAMPLE 9

4-[(4-Fluorophenyl)[(4-fluorophenyl)amino]methyl]-N-methyl-1-piperidinecarboxamide A mixture of 1.91 g (6.25 mmol) of the N,α-bis(4-fluorophenyl)-4-piperidinemethanamine and 0.45 g (7.9 mmol) of methyl isocyanate in 300 mL of CH₂Cl₂ was stirred at room temperature overnight. The solvent was removed in vacuo, and the residue was subjected to flash column chromatography (silica gel, gradiently eluted with 1 to 4% CH₃OH in CH₂Cl₂) to give 1.54 g (68.6%) of white solid, mp 86°–90° C.

Analysis calculated for: $C_{20}H_{23}N_3OF_2$: C, 66.84; H, 6.45; N, 11.69. Found: C, 66.63; H, 6.49; N, 11.73.

EXAMPLE 10

4-[(4-Fluorophenyl)[(4-fluorophenyl)amino]methyl]-N-phenyl-1-piperidine carboxamide A solution of 2.20 g (7.28 mmol) of N,α-piperidinemethanamine and 0.88 g (7.40 mmol) of phenyl isocyanate in 300 mL of CH₂Cl₂ was stirred at room temperature for 16 h. The solution was extracted with dilute NaOH and was dried (Na₂SO₄). The solvent was removed in vacuo. The residue was subjected to flash chromatography (silica gel, elution witgh 1% CH₃OH in CH₂Cl₂), which gave 2.71 g (88.3%) of the title compound as a white crystalline solid, mp 96°–101° C.

Analysis calculated for: $C_{25}H_{25}N_3OF_2$: C, 71.24; H, 5.98; N, 9.976. Found: C, 70.98; H, 5.92; N, 9.95.

EXAMPLE 11

N,α-Bis(4-fluorophenyl)-1-(4-phenylbutyl)-4-piperidinemethanamine dihydrochloride A mixture of 2.10 g (5.6 mmol) of N,α-bis(4-fluorophenyl)4-piperidinemethanamine hydrochloride hydrate, 1.0 g (6.0 mmol) of 4-chlorobutylbenzene and 2.20 g (20.8 mmol) of sodium bicarbonate in 300 mL of 1-butanol was heated at reflux for 16 h. The solvent was removed in vacuo, and the residue was partitioned between CH₂Cl₂ and dilute NaOH. The CH₂Cl₂ solution was dried (Na₂SO₄), and the solvent was removed in vacuo to give an oil. This was subjected to flash chromatography (silica gel, eluted with 4%, CH₃OH in CH₂Cl₂) to give 2.0 g of an oil. This was converted to the HCl salt, and the salt was recrystallized from CH₃OH/ether to give 1.55 g (54.4%) of the title compound as a white crystalline salt, mp 243°–246° C.

Analysis calculated for: $C_{28}H_{32}N_2F_2 \cdot 2HCl$: C, 66.27; H, 6.75; N, 5.52. Found: C, 65.94; H, 6.95; H, 5.50.

EXAMPLE 12

N-[[1-[3-(4-Acetyl-2-methoxyphenoxy)propyl]-4-piperidinyl](4-fluorophenyl)methyl]-N-(4-fluorophenyl)acetamide ethanedioate hydrate (2:2:1)

A solution of 4.51 g (8.9 mmol) of 1-[4-[3-[(4-fluorophenyl)[(4-fluorophenyl)amino]methyl]-1-piperidinyl]-propoxy]-3-methoxyphenyl]ethanone hemihydrate, 1.0 g (13 mmol) of acetyl chloride and 2.0 g (20 mmol) of triethylamine in 250 mL of methylene chloride was stirred at room temperature for 5 days. The solvent was removed in vacuo, and a NMR analysis of the residue indicated that approximately a 60/40 mixture of the product and starting material was present. The material was dissolved in 150 mL of CH₂Cl₂, 1.0 g (12.8 mmol) of acetyl chloride and 0.89 g (8.8 mmol) of triethylamine were added, and the mixture was stirred at room temperature for an additional 5 days. The mixture was poured over ice, and the resulting aqueous mixture was made basic with dilute NaOH. the phases were separated, and the CH₂Cl₂ phase was extracted with dilute NaOH. The organic phase was chilled (Na₂SO₄), and the solvent was removed in vacuo. The residue was subjected to flash chromatography (silica gel, eluted with 2–4% CH₃OH in CH₂Cl₂) to give the free base of the product. This was converted to the oxalate salt, and the salt was recrystallized from CH₃OH/diethyl ether to give 1.02 g (17.6%) of the title compound as a white, crystalline solid, mp 166.5–167.5 dec.

Analysis calculated for: $C_{32}H_{36}N_2O_4 \cdot C_2O_4 \cdot 0.5H_2O$: C, 62.86; H, 6.05; H, 4.31. Found: C, 63.22; H, 5.88; N, 4.09.

EXAMPLE 13

1-[3-[4-(1,1-Dimethylethyl)phenoxy]propyl]-N,α,bis(4-fluorophenyl)-4-piperidinemethanamine hemihydrate A mixture of 2.49 g (0.011 mol) of 1-(p-t-butylphenoxy)-3-chloropropane, 3.10 g (0.0103 mol) of N,α-bis(4-fluorophenyl)-4-piperidinemethanamine, 2.0 g (0.019 mol) of sodium carbonate, and 0.5 g (0.003 mol) of potassium iodide in 400 mL of 1-butanol was heated at reflux for 29 h. The solvent was removed in vacuo, and the residue was partitioned between CH₂Cl₂ and dilute NaOH. The organic phase was dried (Na₂SO₄), and solvent was removed in vacuo to give an oil. The oil was subjected to flash chromatography (silica gel, eluted with 1–3% CH₃OH in CH₂Cl₂) to give 2.79 g (55%) of the title compound as an oil.

Analysis calculated for: $C_{31}H_{38}N_2OF_2 \cdot 0.5H_2O$: C, 64.80; H, 7.19; N, 4.88. Found: C, 65.02; H, 7.12; N, 4.91.

EXAMPLE 14

4-[3-[4-[(4-Fluorophenyl)amino]methyl]-1-piperidinyl]propoxy]benzoic acid 1,1-dimethylethyl ester hemihydrate A mixture of the N,α-bis(4-fluorophenyl)-4-piperidinemethanamine (6.70 g, 0.022 mol), 4-(3-chloropropoxy)benzoic acid 1,1-dimethylethyl ester (5.99 g, 0.022 mol), and potassium carbonate (5.53 g, 0.04 mol) was heated 16 h at reflux in 400 mL of 1-butanol containing sodium iodide (0.2 g). The mixture was concentrated to dryness and partitioned between chloroform and water. The chloroform layer was dried (Na₂SO₄) and filtered, and the solvent was removed to obtain a dark brown oil. This oil was dissolved in methylene chloride and placed on top of a silica gel column. Flash chromatography was carried out using 10% acetone-methylene chloride, 20% acetone-methylene chloride, and 50% acetone-methylene chloride for elution. Fractions of similar purity were combined, and solvents removed to give an oil. This oil was dried in vacuo 16 h at 100° C. This entire process furnished 7.17 g (59.7%) of the title compound as a glass-like material.

Analysis calculated for: $C_{32}H_{38}N_2O_3F_2 \cdot 0.5H_2O$: C, 70.44; H, 7.20; N, 5.13. Found: C, 70.84, H, 7.13, N, 5.19.

EXAMPLE 15

N,α-Bis(4-fluorophenyl)-1-(2-naphthalenylmethyl)-4-piperidinemethanamine

A mixture of N,α-bis(4-fluorophenyl)-4-piperidinemethanamine (6.47 g, 0.0214 mol), 2-(bromomethyl)naphthalene (4.74 g, 0.0214 mol), and potassium carbonate (4.84 g, 0.035 mol) was heated 16 h at reflux in 400 mL of 1-butanol containing sodium iodide (0.2 g). The reaction mixture was concentrated to dryness. The residue was partitioned with 5% sodium hydroxide. The chloroform layer was dried (Na₂SO₄), filtered, and concentrated to give a dark brown oil. The oil was dissolved in methylene chloride and subjected to flash chromatography. Elution was accomplished using methylene chloride, 1% acetone-methylene chloride, 2% acetone-methylene chloride, 5% acetone-methylene chloride, and 10% acetone-methylene chloride. Fractions of similar purity were combined, and solvents were removed to give a viscous gum. This material was dried in vacuo 16 h at 100° C. in the presence of phosphorus pentoxide. This procedure provided 3.40 g (36%) of white glass-like material.

Analysis calculated for: $C_{29}H_{28}N_2F_2$: C, 78.71; H, 6.38; N, 6.33. Found: C, 78.64; H, 6.54; N, 6.38.

EXAMPLE 16

N-[2-(Diethylamino)ethyl]-4-[(4-fluorophenyl)[(4-fluorophenyl)amino]methyl]-1-piperidinecarboxamide hemihydrate A solution of N,N-diethylethylenediamine (1.63 g, 0.014 mol) and 1,1'-carbonyldiimidazole (2.43 g, 0.015 mol) in 100 mL of tetrahydrofuran was stirred at room temperature under nitrogen for 2 h. A solution of N,α-bis(4-fluorophenyl)-4-piperidinemethanamine (3.76 g, 0.01245 mol) was added. The resulting solution was heated at reflux 16 h under nitrogen. The solution was cooled to room temperature and concentrated to dryness. The brown residue obtained was dissolved in methylene chloride. The methylene chloride layer was extracted with water, dried (Na₂SO₄), and filtered. The methylene chloride was removed with a rotary evaporator to give a dark brown oil (5.63 g). This material was dissolved in methylene chloride and placed on a silica gel column for flash chromatography. The column was eluted with 20% methanol-ethyl acetate, 50% methanol-ethyl acetate, and methanol. Fractions of similar purity were combined and solvents removed to give a dark brown oil. This material was dried for 16 h at 100° C. in the presence of phosphorus pentoxide. The procedure provided 4.21 g (74.2%) of a dark brown glass.

Analysis calculated for: $C_{25}H_{34}N_4OF_2 \cdot 0.5H_2O$: C, 66.20; H, 7.78; N, 12.32. Found: C, 65.99; H, 7.81; N, 12.49.

EXAMPLE 17

N-α-Bis(4-fluorophenyl)-1-(2-pyrimidinyl)-4-piperidinemethanamine

A mixture of N,α-bis(4-fluorophenyl)-4-piperidinemethanamine (4.76 g, 0.0157 mol), 2-chloropyrimidine (1.80 g, 0.01576 mol), and sodium bicarbonate was heated at reflux for 72 h in 200 mL of ethanol (200). The solvent was removed with a rotary evaporator, and the residue obtained was dissolved in methylene chloride. The methylene chloride layer was extracted with water and 5% sodium hydroxide. The methylene chloride was dried ($Na_2SO_4$) and filtered, and the solvent removed to give a fluffy brownish-gray residue. This material was dissolved in methylene chloride and subjected to flash chromatography on silica gel using methylene chloride, 1% acetone-methylene chloride, 2% acetone-methylene chloride, 5% acetone-methylene chloride, and 10% acetone-methylene chloride for elution. Fractions of similar purity were combined and solvents removed to give a light yellow oil. This material was dried 16 h at 100° C. in vacuo in the presence of phosphorus pentoxide. This process provided 4.07 g (67.9%) of light yellow oil shown to contain 0.25 mole of water.

Analysis calculated for $C_{22}N_{22}N_4F_2 \cdot 0.25H_2O$: C, 68.64; H, 5.89; N, 14.55. Found: C, 68.95; H, 5.82; N, 14.53.

EXAMPLE 18

N,α-Bis(4-fluorophenyl)-1-(2-quinolinylmethyl)-4-piperidinemethanamine ethanedioate hydrate (2:2:1)

A mixture of N,α-bis(4-fluorophenyl)-4-piperidinemethanamine (4.23 g, 0.014 mol), 2-(chloromethyl)quinoline monohydrochloride (3.00 g, 0.014 mol), and sodium bicarbonate (2.42 g, 0.029 mol) was stirred 32 h at room temperature in 350 mL of ethanol (200). The reaction was concentrated to dryness, and the residue obtained was dissolved in chloroform. The chloroform layer was extracted with water. The chloroform layer was dried ($Na_2SO_4$) and filtered. When the chloroform was removed by rotary evaporator, a dark brown oil was obtained. This oil was dissolved in methylene chloride and subjected to flash chromatography on silica gel. Elution was accomplished using methylene chloride, 1% methanol-methylene chloride, and 2% methanol-methylene chloride. Fractions of similar purity were combined, and the solvents were removed to give a brown oil. Attempts to prepare a crystalline HCl salt gave a substance which was extremely hydroscopic. This material was converted to the free base and subjected again to flash chromatography using the same solvent systems for elution. A brown oil was obtained and converted to the oxalate salt in methanol-diethyl ether. A white solid was isolated and dried in vacuo 16 h at 100° C. This process furnished 1.36 g (17.9%) of white crystalline solid, mp 180°–182° C.

Analysis calculated for $C_{20}H_{27}N_3OF_2 \cdot C_2H_2O_4 \cdot 0.5H_2O$: C, 66.41; H, 5.57; N, 7.74. Found: C, 66.77; H, 5.40; N, 7.70.

EXAMPLE 19

1-Benzoyl-N,α-bis(4-fluorophenyl)-4-piperidinemethanamine

A solution of N,α-bis(4-fluorophenyl)-4-piperidinemethanamine (3.21 g, 0.0106 mol), triethylamine (2.5 g, 0.025 mol), and benzoyl chloride (1.70 g, 0.012 mol) in 400 mL of methylene chloride was stirred 16 h at room temperature. The reaction was concentrated to dryness and dissolved in chloroform. The chloroform layer was extracted successively with water, 1N sulfuric acid, and 5% sodium hydroxide. The chloroform layer was dried ($Na_2SO_4$) and filtered. The chloroform was removed to give a fluffy-white residue. This material was dissolved in methylene chloride and chromatographed by flash chromatography on silica gel. Elution was accomplished using methylene chloride, 1% acetone-methylene chloride, 2% acetone-methylene chloride, and 4% acetone-methylene chloride. Fractions of similar purity were combined, and solvents removed to give a fluffy-white residue. This material was triturated with isopropyl ether and chilled in a freezer. A white solid was isolated and dried, 16 h at 78° C. This furnished 1.40 g (32.5%) of white crystalline solid, mp 157°–158° C.

Analysis calc'd for: $C_{25}H_{24}N_2OF_2$: C, 73.87; H, 5.95; N, 6.89. Found: C, 73.60; H, 5.88; N, 6.82.

EXAMPLE 20

N,α-Bis(4-Fluorophenyl)-1-[2(2-naphthalenyloxy)ethyl]-4-piperidinemethanamine hydrochloride (1:2)

A mixture of N,α-bis(4-fluorophenyl)-4-piperidinemethanamine (3.42 g, 0.0113 mol), 2-bromoethyl naphthyl ether (2.83 g, 0.0113 mol), and potassium carbonate (3.46 g, 0.025 mol) was heated at reflux 16 h in 350 mL of 1-butanol containing sodium iodide (0.2 g). The reaction was concentrated to dryness, and the residue partitioned between chloroform and water. The chloroform layer was extracted with 5% sodium hydroxide. The organic layer was dried ($Na_2SO_4$) and filtered. The chloroform was removed by rotary evaporator to give a brown residue. This material was subjected to flash chromatography on silica gel. Elution was accomplished using methylene chloride, 1% methanol-methylene chloride, and 2% methanol-methylene chloride. Fractions of similar purity were combined and solvents removed. A brown residue was obtained and converted to the HCl salt in methanol-diethyl ether and placed in the freezer. A white solid was isolated and dried 16 h at 78° C. This process provided 2.24 g (36.3%) of white crystalline product mp 226°–230° C. (dec.).

Analysis calc'd for: $C_{30}H_{30}N_2OF_2 \cdot 2HCl$: C, 66.06; H, 5.91; N, 5.14. Found: C, 65.81; H, 5.92; N, 5.10.

EXAMPLE 21

(+)-N,α-Bis(4-fluorophenyl)-4-piperidinemethanamine hydrochloride (2:5)

The compound of Preparation 29 (3.0 g, 0.0047 mole) was dissolved in methanol (30 mL). The stirred solution was treated with concentrated hydrochloric acid (30 mL) and the mixture heated at 50° C. for 4 h. The mixture was stirred at room temperature under a nitrogen atmosphere for 18 hr. The mixture was partially concentrated to remove the methanol and the remaining solution diluted with water (100 mL). Some insoluble material was removed by filtration and the filtrate washed several times with methylene chloride. The aqueous solution was basified with 50% sodium hydroxide solution and extracted with a 1:1 mixture of ethyl acetate-acetonitrile. The aqueous layer was acidified, washed with methylene chloride, basified, and again extracted with 1:1 ethyl acetate-acetonitrile. The extracts were combined, concentrated, and the residue dissolved in absolute ethanol. After filtration to remove some solid, the filtrate was treated with a solution of HCl in 2-propanol. White crystals formed upon trituration which were collected and dried to give 0.48 g (30% yield), mp 215° C. (decomposes), $[\alpha]_D^{22} = +50.5°$ (c=1, MeOH).

Analysis calculated for $C_{18}H_{20}N_2F_2 \cdot 2.5HCl$: C, 54.94; H, 5.76; N, 7.12. Found: C, 54.12: H, 5.95; N, 6.91.

EXAMPLE 22

(−)-N,α-Bis(4-fluorophenyl)-4-piperidinemethanamine hydrochloride (1:3)

Following the procedure of Example 22, a 30 g portion of the compound of Preparation 30 was hydrolyzed, isolated and the hydrochloride salt prepared to obtain 0.25 g (15%), mp 208°–212° C. (decomposes), $[\alpha]_D^{22} = -41.1°$ (c=1, MeOH).

Analysis calculated for: $C_{18}H_{20}N_2F_2 \cdot 3HCl$: C, 52.51; H, 5.63; N, 6.80. Found: C, 52.22; H, 5.60; N, 6.58.

EXAMPLE 23

N,α-Bis(4-fluorophenyl)-1-(phenylmethyl)-4-piperidinemethanamine dihydrochloride A mixture of N,α-bis(4-fluorophenyl)-4-piperidinemethanamine (3.30 g, 0.0109 mol), benzylbromide (1.86 g, 0.0109 mol), and sodium bicarbonate (1.68 g, 0.02 mol) was stirred 16 h at room temperature in 300 mL of acetonitrile (dried over 4 A molecular sieves) containing sodium iodide (0.2 g). The mixture was then heated at reflux 16 h followed by stirring 72 h at room temperature. The reaction was stripped to dryness and partitioned between chloroform and water. The chloroform layer was extracted with 5% sodium hydroxide and dried (Na₂SO₄). The chloroform was removed to give a fluffy-brown residue. This material was dissolved in methylene chloride for flash chromatography on a silica gel column. Elution was accomplished using 1% acetone in methylene chloride, 3% acetone in methylene chloride, and 5% acetone in methylene chloride. Fractions of similar purity were combined, and solvents removed to give an oil. This oil was converted to the HCl salt in an ethanol-diethyl ether mixture. The white solid obtained was then recrystallized from methanol-diethyl ether to give a white solid. The solid was dried 16 h at 78° C. in the presence of phosphorus pentoxide. This method provided 1.86 g (36.7%) of white crystalline solid, mp 241°–242° C. (dec.).

Analysis calculated for: $C_{25}H_{26}N_2F_2 \cdot 2HCl$: C, 64.52; H, 6.06; N, 6.02. Found: C, 64.35; H, 6.10; N, 6.05.

EXAMPLE 24

1-[4-[3-[4-[(4-Fluorophenyl)[(4-fluorophenyl)amino]-methyl]-1-piperidinyl]propoxy]phenyl]-2-methyl-1-propanone dihydrochloride A mixture of N,α-bis(4-fluorophenyl)-4-piperidinemethanamine (4.63 g, 0.0153 mol), 1-[4-(3-chloropropoxy)phenyl]-2-methyl-1-propanone (3.69 g, 0.0153 mol), and potassium carbonate (2.76 g, 0.02 mol) was heated at reflux 16 h in 350 mL 1-butanol containing sodium iodide (0.2 g). The reaction was concentrated to dryness and partitioned between chloroform and water. The chloroform layer was then extracted with 5% sodium hydroxide and dried (Na₂SO₄). The chloroform was removed to give a red oil. This material was subjected to flash chromatography on silica gel using 2% methanol in methylene chloride to accomplish elution. Fractions of similar purities were combined, and solvents removed to give an oil. The oil was converted to the HCl salt and recrystallized from methanol-diethyl ether to give a white solid. This solid was dried 16 h at 78° C. in vacuo. The procedure utilized here furnished 5.26 g (59%) of white crystalline product, mp 221°–223° C. (dec.).

Analysis calculated for: $C_{31}H_{36}N_2O_2F_2 \cdot 2HCl$: C, 64.25; H, 6.61; N, 4.83. Found: C, 64.32; H, 6.64; N, 4.99.

EXAMPLE 25

3-[2-[4-[(4-Fluorophenyl)[(4-fluorophenyl)amino]methyl]-1-piperidinyl]ethyl]2,4(1H,3H)quinazolinedione dihydrochloride A mixture of 2.89 g (7.52 mmol) of N,α-bis(4-fluorophenyl)-4-piperidinemethanamine hydrochloride hydrate, 1.74 g (7.75 mmol) of 3-(2-chloroethyl)-2,4(1H,3H)quinazolinedione, 7.56 g (90 mmol) of sodium bicarbonate, and 0.20 g (1.20 mmol) of potassium iodide in 250 mL of 1-butanol was heated at reflux for 20 h. The solvent was removed in vacuo, and the residue was partitioned between CH₂Cl₂ and dilute NaOH. The organic phase was dried (Na₂SO₄), and the solvent was removed in vacuo. The residue was subjected to flash chromatography (silica gel, eluted with 1–3% CH₃OH in CH₂Cl₂) to give the free base of the product. This was converted to the HCl salt, and the salt was recrystallized from CH₃OH/diethyl ether to give 1.80 g (42.7%) of the title compound as a white solid, mp 213°–220° C.

Analysis calculated for: $C_{28}H_{28}N_4O_2F_2 \cdot 2HCl$: C, 59.69; H, 5.37; N, 9.94. Found: C, 59.73; H, 5.32; N, 9.90.

EXAMPLE 26

1-Cyclohexyl-N,α-bis(4-fluorophenyl)-4-piperidinemethamine hydrochloride hydrate (2:4:1)

A mixture of N,α-bis(4-fluorophenyl)-4-piperidinemethanamine (9.34 g, 0.0309271 mol), bromocyclohexane (5.04 g, 0.0309271 mol), and potassium carbonate (6.91 g, 0.05 mol) was heated 16 h at reflux in 350 mL of 1-butanol containing potassium iodide (0.2 g). The butanol was removed by rotary evaporation, and the residue was partitioned between chloroform and water. The chloroform layer was extracted with water and 5% sodium hydroxide. The chloroform layer was dried (Na₂SO₄), filtered, and then concentrated to give a dark brown material. Gas chromatographic analysis of this material showed 91% starting material and 8% of another material. This material was dissolved in methylene chloride and placed on a 300-g silica gel column. Elution was accomplished using methylene chloride, 1% methanol-methylene chloride, 2% methanolmethylene chloride, 2.5% methanol-methylene chloride, 3% methanol-methylene chloride, and 3.5% methanol-methylene chloride. Fractions of similar purity were combined, and solvents were removed to give an oil (0.64 g). This oil was converted to the HCl salt, and the salt was recrystallized from (methanol-diethylether). A white solid was isolated and dried 16 h in vacuo at 78° C. This procedure produced 0.85 g (5.89%) of white crystalline material, mp 245° C. (dec.).

Analysis calculated for $C_{24}H_{30}N_2F_2 \cdot 2HCl \cdot 0.5H_2O$: C, 61.80; H, 7.13; N, 6.01. Found: C, 61.67; H, 7.04; N, 6.05.

EXAMPLE 27

N,α-Bis(4-fluorophenyl)-1-(2-methylpropyl)-4-piperidinemethanamine hydrochloride hydrate (2:4:1)

A mixture of N,α-bis(4-fluorophenyl)-4-piperidinemethanamine (4.87 g, 0.016 mol), 1-bromo-2-methylpropane (2.21 g, 0.016 mol), and sodium bicarbonate (2.52 g, 0.03 mol) was stirred 72 hr under nitrogen in 250 mL of anhydrous acetonitrile. The reaction was heated at reflux 4 hr and then cooled to room temperature. The reaction was concentrated to dryness and partitioned between chloroform and water. The chloroform layer was extracted with 5% sodium hydroxide, dried ($Na_2SO_4$) and filtered. The chloroform was removed to give a dark brown oil. This oil was subjected to flash chromatography on silica gel using methylene chloride and mixtures of methylene chloride-methanol for elution. Fractions of similar purity were combined, and solvents were removed to give a brown oil. This oil was converted to the hydrochloride and the salt was recrystallized from 2-propanol. A white solid was obtained and washed with diethyl ether. The white solid was dried in vacuo at 78° C. This procedure furnished 1.61 g (21.9%) of white crystalline product, mp 138°–139° C. (dec.) which contained 2-propanol.

Analysis calculated for: $C_{22}H_{28}N_2F_2 \cdot 2HCl \cdot 0.5H_2O \cdot 0.3C_3H_8O$: C, 60.00; H, 7.34; N, 6.11. Found: C, 60.17; H, 7.30; N, 6.19.

EXAMPLE 28

N,α-Bis(4-fluorophenyl)-1-propyl-4-piperidinemethanamine hydrochloride hydrate (2:4:1)

A mixture of N,α-bis(4-fluorophenyl)-4-piperidinemethanamine (4.95 g, 0.0163907 mol), n-propyl iodide (2.79 g, 0.0163907 mol), and sodium bicarbonate (3.36 g, 0.04 mol) was stirred 48 hr at room temperature. The mixture was then heated at reflux 4 h. The reaction was concentrated to dryness and then partitioned between chloroform and water. The chloroform layer was extracted with 5% sodium hydroxide and then dried ($Na_2SO_4$). The chloroform layer was filtered, and the chloroform solvent was removed by a rotary evaporator to give a brown oil. This oil was subjected to flash chromatography on silica gel. Elution was accomplished using mixtures of methanol and methylene chloride. Fractions of similar purity were combined and solvents were removed. The oil obtained was dissolved in methanol and converted to the hydrochloride salt using ethereal HCl. Recrystallization from methanol diethyl ether gave a white solid which was dried 16 h at 78° C. This process provided 3.82 g (54.7%) of white crystalline material, mp 251° C.

Analysis calculated for: $C_{21}H_{26}N_2F_2 \cdot 2HCl \cdot 0.5H_2O$: C, 59.16; H, 6.86; N, 6.57. Found: C, 59.17; H, 6.72; N, 6.58.

EXAMPLE 29

1-(2-Ethoxyethyl)-N,α-bis(4-fluorophenyl)-4-piperidinemethanamine hydrochloride hydrate (2:4:1)

A mixture of N,α-bis(4-fluorophenyl)-4-piperidinemethanamine (3.33 g, 0.011 mol), 2-bromoethyl ethyl ether (1.69 g, 0.011 mol), and sodium bicarbonate (1.68 g, 0.011 mol) was stirred under nitrogen 16 h at room temperature. The mixture was then heated at reflux for 4 h and stirred 16 h at room temperature. The reaction was concentrated to dryness and partitioned between chloroform and water. The chloroform layer was back extracted with 5% sodium hydroxide. The chloroform layer was dried ($Na_2SO_4$), filtered, and the chloroform was removed to give an oil. The oil was subjected to flash chromatography on silica gel using methanol-methylene chloride mixtures for elution. Fractions of similar purity were combined and solvents removed. A brown oil was obtained which crystallized to a brown solid. This material was converted to the hydrochloride salt and the salt was recrystallized from methanol-diethyl ether to give a white solid. The solid was dried 16 h in vacuo at 78° C. This process furnished 2.00 g (39.8%) of white crystalline solid mp 241°–243° C. (dec.).

Analysis calculated for: $C_{22}H_{28}N_2OF_2 \cdot 2HCl \cdot 0.5H_2O$: C, 57.90; H, 6.85; N, 6.14. Found: C, 57.88; H, 6.76; N, 6.14.

EXAMPLE 30

N,α-Bis(4-fluorophenyl)-4-piperidinemethanamine

A stirred mixture of 4-(4-fluorobenzoyl)piperidine hydrochloride (40.0 g, 0.164 mole), 4-fluoroaniline (22.0 g, 0.197 mole), and benzenesulfonic acid (0.14 g) in xylenes (820 mL) was heated at reflux temperature for 18 hr during which time 3 mL of water was collected in a Dean-Stark trap. After cooling to 50° C., sodium borohydride (12.5 g, 0.328 mole) was added slowly. Ethanol (100 mL) was added and the mixture heated at 60° C. for 1 h. After stirring for 18 h under a nitrogen atmosphere at room temperature, the mixture was chilled to 5° C. with an ice bath and chilled water added cautiously. A rapid evolution of gas occurred causing a portion of the reaction mixture to spill over into the ice bath. The contents of the ice bath and the remainder of the reaction mixture were combined and basified with 50% sodium hydroxide solution, causing a viscous insoluble oil to separate from the mixture. The material was dissolved in ethyl acetate. The ethyl acetate solution and the xylene layer were combined and washed with additional dilute aqueous NaOH solution. The aqueous layers were combined and extracted with ethyl acetate-acetonitrile (60:40). The organic layers were combined and extracted twice with 300 mL portions of 3N HCl solution. The acid extract was basified with 50% sodium hydroxide solution and extracted twice with 600 mL portions of ethyl acetate-acetonitrile (60:40). The extracts were combined, treated with charcoal, dried ($MgSO_4$), and concentrated. The residual material was heated at 100° C. under vacuum for 1 h to remove excess 4-fluoroaniline. The yield was 24.8 g (50.5%).

EXAMPLE 31

4-[[(3,4-Difluorophenyl)amino](4-fluorophenyl)methyl]piperidine hydrochloride hydrate (1:2:1)

A mixture of 50.7 g (0.21 mol) of 4-(4-fluorobenzoyl)-piperidine hydrochloride, 40.0 g (0.31 mol) of 3,4-difluoroaniline and 0.80 g (0.0051 mol) of benzenesulfonic acid in 1 L of xylenes was heated at reflux for 4 days with water being removed with Dean-Stark trap. The mixture was cooled to room temperature and 500 mL of dry THF was added. The mixture was cooled in an ice bath and was swept with a stream of nitrogen. To this mixture was slowly added 40.0 g (1.1 mol) of LiAlH$_4$, and the mixture was stirred mechanically at room temperature overnight. Dilute NaOH was added slowly over 1 h, and the resulting mixture was filtered through a pad of Celite. The solvent was removed from the filtrate in vacuo, and the residue was partitioned between CH$_2$Cl$_2$ and water. The CH$_2$Cl$_2$ solution was dried (Na$_2$SO$_4$), and the solvent was removed in vacuo. The residue was dissolved in CH$_3$OH, an excess of ethereal HCl was added, and anhydrous ether was added until the solution became cloudy. The solution stood at room temperature overnight and 28.72 g (33.3%) of product was collected. The filtrate yielded an additional 4.51 g (5.2%) of product. A small portion of this was recrystallized from CH$_3$OH/ether to give an analytically pure sample of the title compound as a white crystalline solid, mp 210°–213° C.

Analysis calculated for: C$_{18}$H$_{19}$N$_2$F$_3$.2HCl.H$_2$O: C, 52.57; H, 5.64; N, 6.81. Found: C, 52.93; H, 5.61; N, 6.83.

EXAMPLE 32

N-(3,4-Difluorophenyl)-α-(4-fluorophenyl)-1-(3-phenoxypropyl)-4-piperidinemethanamine ethanedioate (1:1)

A mixture of 4-[[(3,4-difluorophenyl)amino](4-fluorophenyl)methyl]piperidine (6.15 g, 0.015 mol), phenoxypropyl bromide (3.23 g, 0.015 mol), and potassium carbonate (6.22 g, 0.045 mol) was heated at reflux 16 hr in 1-butanol containing sodium iodide (0.2 g). The reaction was concentrated to dryness and the residue obtained was partitioned between chloroform and water. The chloroform layer was dried (Na$_2$SO$_4$) and filtered. When the chloroform was removed by rotary evaporation, a brown oil was obtained. This oil was dissolved in methylene chloride and subjected to flash chromatography on silica gel. Elution was carried out using methylene chloride, 1% methanol-methylene chloride, and 2% methanol-methylene. Fractions of similar purity were combined, and solvents were removed to give an oil. The oil was converted to oxalate salt in methanol-diethyl ether. A white solid was isolated and dried in vacuo at 100° C. for 16 hr. This process furnished 4.76 g (58.3%) of white crystalline solid, mp (89° C. glass; 157° C. melted).

Analysis calculated for: C$_{27}$H$_{29}$N$_2$OF$_3$.C$_2$H$_2$O$_4$: C, 63.96; H, 5.74; N, 5.14. Found: C, 63.62; H, 5.71; N, 5.16.

EXAMPLE 33

N-(3,4-Difluorophenyl)-α-(4-fluorophenyl)-1-(2-quinolinylmethyl)-4-piperidinemethanamine ethanedioate hydrate (2:2:1)

A mixture of 3.60 g (8.8 mmol) of 4-[[(3,4-difluorophenyl)amino](4-fluorophenyl)methyl]piperidine hydrochloride hydrate, 2.04 g (9.5 mmol) of 2-chloromethylquinoline and 3.0 g (28.3 mmol) of sodium carbonate in 200 mL of absolute ethanol was stirred at room temperature for 66 h. The solvent was removed in vacuo to give an oil. This was partitioned between CH$_2$Cl$_2$ and dilute NaOH. The CH$_2$Cl$_2$ solution was dried (Na$_2$SO$_4$), and the solvent was removed in vacuo to give an oil. A solution of the oil in methanol was treated with an excess of oxalic acid. Anhydrous ether was added, and 2.53 g (51.3%) of title compound was collected as a crystalline solid, mp. 139°–140° C.

Analysis calculated for: C$_{28}$H$_{26}$N$_3$F$_3$.C$_2$H$_2$O$_4$.0.5-H$_2$O: C, 64.28; H, 5.21; N, 7.50. Found: C, 64.20; H, 4.98; N, 7.41.

EXAMPLE 34

N-(3,4-Difluorophenyl)-α-(4-fluorophenyl)-1-(2-naphthalenylmethyl)-4-piperidinemethanamine dihydrochloride A mixture of 3.10 g (7.5 mmol) of 4-[[(3,4-difluorophenyl)amino](4-fluorophenyl)methyl]piperidine hydrochloride hydrate, 1.70 g (7.7 mmol) of 2-bromomethylnaphthalene and 5.1 g (60.7 mmol) of sodium bicarbonate in 200 mL of absolute ethanol was stirred at room temperature for 20 h. The solvent was removed in vacuo, and the residue was partitioned between methylene chloride and dilute NaOH. The organic phase was dried (Na$_2$SO$_4$), and the solvent was removed in vacuo. The residue was subjected to flash chromatography (silica gel, elution with 1–4% MeOH in CH$_2$Cl$_2$) to give an oil. This was converted to the HCl salt, and the salt was recrystallized from a mixture of methanol and diethylether to give 1.53 g (38.3%) of the title compound as a crystalline solid, mp 187°–190° C.

Analysis calculated for: C$_{29}$H$_{27}$N$_2$F$_3$.2HCl.0.25H$_2$O: C, 64.75; H, 5.53; N, 5.21. C, 64.82; H, 5.41; N, 5.23.

EXAMPLE 35

N-(3,4-Difluorophenyl)-α-(4-fluorophenyl)-1-[2-(2-naphthalenyloxy)ethyl]-4-piperidinemethanamine dihydrochloride A mixture of 4.20 g (0.010 mol) of 4-[[(3,4-difluorophenyl)amino](4-fluorophenyl)methyl]piperidine, 2.90 g (0.012 mol) of 2-(2-bromoethoxy)naphthalene, 8.1 g (0.096 mol) of sodium bicarbonate, and a trace of sodium iodide in 400 mL of 1-butanol was heated at reflux for 16 h. The solvent was removed in vacuo, and the residue was partitioned between CH$_2$Cl$_2$ and dilute NaOH. The CH$_2$Cl$_2$ solution was dried (Na$_2$SO4), and the solvent was removed in vacuo to give a gum. This was subjected to flash column chromatography (silica gel, eluted with CH$_2$Cl$_2$ and 1–2% MeOH in CH$_2$Cl$_2$) to give the free base. This was converted to the HCl salt, and the salt was recrystallized from diethyl ether/MeOH to give 3.05 g (54.1%) as a white crystalline solid: mp 210°–215° C.

Analysis calculated for: C$_{30}$H$_{29}$N$_2$F$_3$O.2HCl: C, 63.95; H, 5.55; N, 4.97. Found: C, 63.90; H, 5.55; N, 4.93.

EXAMPLE 36

α-(4-Fluorophenyl)-N-[(4-fluorophenyl)methyl]-4-piperidinemethanamine hydrochloride hydrate (2:4:3)

A mixture of 9.54 g (0.021 mol) of the α-(4-fluorophenyl)-N-[(4-fluorophenyl)methyl]-1-phenylfulfonyl-4-piperidinemethaneamine, 8.20 g (0.087 mol) of phenol and 150 mL of 48% HBr was heated at reflux for 8 h. The reaction was poured over ice, and the mixture was made basic with 50% NaOH. The basic mixture was extracted with CH$_2$Cl$_2$, and the CH$_2$Cl$_2$ extract was dried (Na$_2$SO$_4$). The solvent was removed in vacuo to give an oil. This was dissolved in CH$_3$OH, treated with 4.87 g (0.042 mol) of fumaric acid, and anhydrous ether was added. This produced 7.69 g of a white solid, which was partitioned between CH$_2$Cl$_2$ and dilute NaOH. The CH$_2$Cl$_2$ solution was dried (Na$_2$SO$_4$), and the solvent was removed in vacuo. The residue was dissolved in CH$_3$OH, excess ethereal HCl was added, and 2.24 g (25.1%) of the title compound was collected as a white solid, mp 238°–240° C.

Analysis calculated for: $C_{19}H_{27}N_2F_2Cl_2$: C, 54.81; H, 6.54; N, 6.73. Found: C, 54.93; H, 6.11; N, 6.72.

EXAMPLE 37

α-(4-Fluorophenyl)-N-[(4-fluorophenyl)methyl]-1-(2-phenylethyl)-4-piperidinemethanamine (E)-2-butenedioate (2:3)

A mixture of 11.4 g (0.037 mol) of N-(2-phenylethyl)-4-(4-fluorobenzoyl)piperidine, 6.79 g (0.054 mol) of 4-fluorobenzylamine and 0.54 g (0.0034 mol) of benzenesulfonic acid in 400 mL of xylene was heated at reflux for 24 h. Water was removed from the reaction mixture with a Dean-Stark trap. The solvent was removed in vacuo, and the residue was partitioned between $CH_2Cl_2$ and dilute NaOH. The $CH_2Cl_2$ solution was dried ($Na_2SO_4$), and the solvent was removed in vacuo to give 12.46 g (81.2%) a-(4-fluorophenyl)-N-[(4-fluorophenyl)methyl]-1-(2-phenylethyl)-4-piperidinemethanimine as an oil.

A mixture of 7.85 g (0.0188 mol) of α-(4-fluorophenyl)-N-[(4-fluorophenyl)methyl]-1-(2-phenylethyl)-4-piperidinemethanimine and 1.30 g (0.034 mol) of lithium aluminum hydride in 200 mL of dry THF (distilled from sodium-benzophenone ketyl) and under an atmosphere of nitrogen was stirred at room temp for 14 h. A solution of 5% NaOH was added dropwise to the mixture and 20 mL of water was added. Methylene chloride was added and the mixture was filtered through Celite. The filtrate was extracted with water and was dried ($Na_2SO_4$). The solvent was removed in vacuo to give an oil. This was dissolved in methanol, treated with 4.41 g (0.038 mol) of fumaric acid, and anhydrous ether was added. A precipitate formed to give 7.45 g (65.4%) of the title compound as a white solid, mp 177°-179° C.

Analysis calculated for: $C_{33}H_{37}N_2F_2O_{6.5}$: C, 65.66; H, 6.18; N, 4.64. Found: C, 65.65; H, 6.06; N, 4.63.

EXAMPLE 38

N[(4-Fluorophenyl)methyl]-N-[(4-fluorophenyl)[1-(2-phenylethyl)-4-piperidinyl]methyl]acetamide (E)-2-butendioate (1:1) monohydrate A mixture of 1.37 g (3.25 mmol) of α-(4-fluorophenyl)-N-[(4-fluorophenyl)methyl]-1-(2-phenylethyl)-4-piperidinemethanamine, 1.0 g (13 mmol) of acetyl chloride and 0.90 g (9 mmol) of triethylamine in 150 mL of $CH_2Cl_2$ was stirred at room temp for 16 h. The reaction mixture was poured over ice. The mixture was then extracted with the following in sequence: dilute NaOH, dilute $H_2SO_4$ and dilute NaOH. The $CH_2Cl_2$ solution was dried ($Na_2SO_4$), and the solvent was removed in vacuo to give an oil. This was treated with a methanolic solution of fumaric acid, ether was added, and a precipitate was collected to give 1.0 g (51.6%) of the title compound as a white crystalline solid, mp 206°-208° C., dec.

Analysis calculated for: $C_{33}H_{36}N_2O_6F_2$: C, 66.43; H, 6.42; N, 4.70. Found: C, 66.60; H, 6.12; N, 4.69.

EXAMPLE 39

N-[(4-Fluorophenyl)methyl]-N-[(4-fluorophenyl)[1-(2-phenylethyl)-4-piperidinyl]methyl]-N'-methylurea (E)-2-butenedioate (2:3)

A mixture of 1.37 g (0.0033 mol) of the α-(4-fluorophenyl)-N-[(4-fluorophenyl)methyl]-1-(2-phenylethyl)-4-piperidinemethanamine and 1.0 g (0.0175 mol) of methyl isocyanate in 150 mL of $CH_2Cl_2$ was stirred at room temperature overnight. The reaction mixture was extracted with water and was dried ($Na_2SO_4$). The solvent was removed in vacuo, and the residue was converted to the fumarate salt. The salt was recrystallized from $CH_3OH$/ether to give 1.62 g (76.5%) of a white solid, mp 136°-140° C.

Analysis calculated for: $C_{35}H_{39}N_3O_7F_2$: C, 64.51; H, 6.03; N, 6.45. Found: C, 64.92; H, 6.15; N, 6.75.

EXAMPLE 40

α-(4-Fluorophenyl)-N-[(4-fluorophenyl)methyl]-1-(3-phenoxypropyl-4-piperidinemethanamine dihydrochloride hemihydrate A solution of 20.23 g (59 mmol) of 4-(p-fluorobenzoyl)-1-(3-phenoxypropyl)piperidine, 9.80 g (78 mmol) of 4-fluorobenzylamine and 1.0 g (7.9 mmol) of benzenesulfonic acid in 500 mL of xylene was heated at reflux for 5 days with water being removed from the reaction mixture with a Dean-Stark trap. The solvent was removed in vacuo, and the residue was partitioned between $CH_2Cl_2$ and dilute NaOH. The $CH_2Cl_2$ solution was dried ($Na_2SO_4$), and the solvent was removed in vacuo to give a gum. This was reacted for 16 h with 8.1 g (210 mmol) of $LiAlH_4$ in 500 mL of THF at room temperature and under an atmosphere of nitrogen. Dilute NaOH was then added followed by the addition of 100 mL of water. $CH_2Cl_2$ was added, and the mixture was filtered through Celite. The phases were separated, and the organic phase was extracted with several portions of water. The organic phase was dried ($Na_2SO_4$), and the solvent was removed in vacuo to give an oil. This was dissolved in methanol, excess ethereal HCl was added, and anhydrous ether was added until the solution became cloudy. A white precipitate was collected to give 14.44 g (46.0%) of white, crystalline solid, mp 236°-237° C.

Analysis calculated for: $C_{28}H_{35}N_2O_{1.5}F_2Cl_2$: C, 63.16; H, 6.63; N, 5.26. Found: C, 63.41; H, 6.60; N, 5.31.

EXAMPLE 41

1-[4-[3-[4-[(4-Fluorophenyl)[[(4-fluorophenyl)methyl]amino]methyl]-1-piperidinyl]propoxy]-3-methoxyphenyl]ethanone dihydrochloride hemihydrate A mixture of 3.03 g (7.81 mmol) of α-(4-fluorophenyl)-N-[(4-fluorophenyl)methyl]-4-piperidinemethanamine hydrochloride hydrate, 1.95 g (8.1 mmol) of 3-chloro-1-(4-acetyl-2-methoxyphenoxy)propane and 2.86 g (27 mmol) of sodium carbonate in 400 mL of 1-butanol was heated at reflux for 16 h. The solvent was removed in vacuo, and the residue was partitioned between $CH_2Cl_2$ and dilute NaOH. The $CH_2Cl_2$ solution was dried ($Na_2SO_4$), and the solvent was removed in vacuo to give an oil. This was subjected to flash chromatography (silica gel, 3% $CH_3OH$ in $CH_2Cl_2$) to give 2.26 g of an oil. The oil was converted to the hydrochloride salt, and the salt was recrystallized from methanol/ether to give 2.03 g (43%) of the title compound as a crystalline solid, mp 239°-240° C.

Analysis calculated for: $C_{31}H_{39}N_2O_{3.5}F_2Cl_2$: C, 61.59; H, 6.50; N, 4.63. Found: C, 61.50; H, 6.40; N, 4.62.

EXAMPLE 42

4-[(4-Fluorophenyl)[[(4-fluorophenyl)methyl]amino]methyl]-N-methyl-1-piperidinecarboxamide (E)-2-butendioate (1:1)

A solution of 3.57 g (9.20 mmol) of α-(4-fluorophenyl)-N-[(4-fluorophenyl)methyl]-4-piperidinemethanamine and 0.68 g (12.0 mmol) of methyl isocyanate in 400 mL of $CH_2Cl_2$ was stirred at room temperature overnight. The solvent was removed in vacuo to give as an oil. This was converted to the fumarate salt, and the salt was recrystallized from methanol/ether to give 0.96 g (21.3%) of the title compound as a white crystalline solid, mp 101°–105° C. A second crop of solid was collected from the filtrate to give 1.24 g (27.0%) of the monohydrate of the title compound, mp 98°–102° C.

Analysis of calculated for: $C_{25}H_{29}N_3O_5F_2$: C, 61.34; H, 5.97; N, 8.58. Found: C, 61.22; H, 6.10; N, 8.84.

Analysis calculated for: $C_{25}H_{29}N_3O_5F_2 \cdot 0.5H_2O$: C, 60.23; H, 6.07; N, 8.43. Found: C, 60.10; H, 6.06; N, 8.85.

EXAMPLE 43

N-[(4-Fluorophenyl)methyl]-N-[(4-fluorophenyl)[1-[(methylamino)carbonyl]-4-piperidinyl]methyl]-N'-methylurea A solution of 2.06 g (6.5 mmol) of α-(4-fluorophenyl)-N-[(4-fluorophenyl)methyl]-4-piperidinemethanamine and 3.1 g (54.4 mmol) of methyl isocyanate in 300 mL of $CH_2Cl_2$ was stirred at room temperature for 18 h. The solvent was removed in vacuo to give a white solid. The solid was recrystallized from methylene chloride/ether to give 2.65 g (94.8%) of a white, crystalline solid containing 0.15 mole of $CH_2Cl_2$, mp 120°–162° C.

Analysis calculated for: $C_{23}H_{28}N_4O_2F_2 + 0.15CH_2Cl_2$: C, 62.73; H, 6.44; N, 12.64. Found: C, 62.73; H, 6.48; N, 12.57.

EXAMPLE 44

N-[(4-Fluorophenyl)methyl]-N-[(4-fluorophenyl)[1-(3-phenoxypropyl)-4-piperidinyl]methyl]acetamide (E)-2-butenedioate (1:1)

A solution of 2.21 g (4.2 mmol) of the compound of Example 40, 0.59 g (7.5 mmol) of acetyl chloride, and 1.0 g (9.9 mmol) of triethylamine in 300 mL of $CH_2Cl_2$ was stirred at room temperature for 104 h. The solution was extracted with several portions of dilute NaOH and was dried ($Na_2SO_4$). The solvent was removed in vacuo to give an oil. The oil was reacted with excess fumaric acid in $CH_3OH$. Excess anhydrous ether was added, and 2.19 g (85.7%) of the title compound was collected as a white, crystalline solid, mp 141°–143° C.

Analysis calculated for: $C_{34}H_{38}N_2O_6F_2$: C, 67.09; H, 6.29; N, 4.60. Found: C, 67.05; H, 6.31; N, 4.60.

EXAMPLE 45

N-[(4-Fluorophenyl)methyl]-N-[(4-fluorophenyl)[(-phenylamino)carbonyl]-4-piperidinyl]methyl]-N'-phenylurea A solution of 1.55 g (4.9 mmol) of N,α-bis(4-fluorophenyl)-4-piperidinemethanamine and 1.43 g (12.0 mmol) of phenyl isocyanate in 300 mL of $CH_2Cl_2$ was stirred at room temperature overnight. The solvent was removed in vacuo, and the residue was recrystallized from $CH_2Cl_2$/ether to give 2.32 g (85.4%) of white, crystalline solid, mp 229°–230° C.

Analysis calculated for: $C_{33}H_{32}N_4O_2F_2$: C, 71.46; H, 5.82; N, 10.10. Found: C, 71.15; H, 5.83; N, 10.02.

EXAMPLE 46

α-(4-Fluorophenyl)-N-(2-phenylethyl)-4-piperidinemethanamine (E)-2-butenedioate (1:2) hemihydrate A mixture of 2.15 g (4.8 mmol) of α-(4-fluorophenyl)-N-(2-phenylethyl)-1-(phenylsulfonyl)-4-piperidinemethanamine and 3.5 g (37 mmol) of phenol in 60 mL of 48% HBr was refluxed for 3 h and then was stirred at ambient temperature for 14 h. The mixture was poured over ice, and the mixture was made basic with 50% NaOH. The basic mixture was extracted with $CH_2Cl_2$. The $CH_2Cl_2$ solution was dried ($MgSO_4$), and the solvent was removed in vacuo to give an oil. This was dissolved in $CH_3OH$, 2 equivalents of fumaric acid was added, and ether was added. A white precipitate was collected to give 1.59 g (59.8%) of the title compound as a white, crystalline solid, mp 189.5°–191° C.

Analysis calculated for: $C_{28}H_{34}N_2FO_{8.5}$: C, 60.75; H, 6.19; N, 5.06. Found: C, 60.67; H, 6.01; N, 5.08.

EXAMPLE 47

1-[4-[3-[4-[(4-Fluorophenyl)[(2-phenylethyl)amino]methyl]-1-piperidinyl]propoxy]-3-methoxyphenyl]ethanone (E)-2-butenedioate (1:1) monohydrate A mixture of 4.52 g (0.0145 mol of α-(4-fluorophenyl)-N-(2-phenylethyl)-4-piperidinemethanamine, 3.51 g (0.0145 mol) of 3-(4-acetyl-2-methoxyphenoxy)-1-chloropropane, 0.41 g (0.0025 mol) of KI and 8.2 g (0.098 mol) of sodium carbonate in 400 mL of 1-butanol was heated at reflux for 18 h. The solvent was removed in vacuo to give an oil. To a solution of this oil in 100 mL of $CH_3OH$ was added 3.40 g (0.029 mol) of fumaric acid. A precipitate was collected. This was recrystallized from $CH_3OH$-ether to give 5.77 g (61%) of white solid, mp 70°–74° C.

Analysis calculated for: $C_{36}H_{45}N_2O_8F$: C, 66.24; H, 6.95; N, 4.29. Found: C, 66.10; H, 6.73; N, 4.33.

EXAMPLE 48

4-[(4-Fluorophenyl)[(2-phenylethyl)amino]methyl]-N-phenyl-1-piperidinecarboxamide (E)-2-butenedioate (4:3)hemihydrate A solution of 2.22 g (7:1 mmol) of α-(4-fluorophenyl)-N-(2-phenylethyl)-4-piperidinemethanamine and 0.87 g (7.3 mmol) of phenyl isocyanate in 100 mL of $CH_2Cl_2$ was stirred at room temperature overnight. Water was added, and the mixture was stirred for 0.5 h. The phases were separated, and the $CH_2Cl_2$ solution was extracted with water. The solution was dried ($Na_2SO_4$), and the solvent was removed in vacuo to give a glass. This was converted to the fumarate salt, and the salt was recrystallized from $CH_3OH$/ether to give 1.79 g (47.8%) of the title compound as a white solid, mp 155°–156.5° C. dec.

Analysis calculated for: $C_{30}H_{34}N_3O_{4.5}F$: C, 68.28; H, 6.50; N, 7.96. Found: C, 68.64; H, 6.21; N, 7.95.

EXAMPLE 49

4-[(4-Fluorophenyl)[(2-phenylethyl)amino]methyl]-N-methyl-1-piperidinecarboxamide (E)-2-butenedioate (2:1) hemihydrate A solution of 1.84 g (5.9 mmol) of α-(4-fluorophenyl)-N-(2-phenylethyl)-4-piperidinemethanamine and 0.28 g (5.1 mmol) of methyl isocyanate in 200 mL of $CH_2Cl_2$ was stirred at room temp overnight. The solvent was removed in vacuo. The residue was dissolved in 30 mL of $CH_3OH$, and 0.68 g (5.9 mol) of fumaric acid was added. The solution was placed in the freezer, and 1.12 g (43.5%) of a white crystalline solid was collected. An additional 0.29 g (11.3%) of solid was collected from the filtrate to give a total of 1.41 g (54.8%) of the title compound as a white solid, mp 104°–107° C.

Analysis calculated for: $C_{24}H_{31}N_3O_{3.5}$: C, 66.04; H, 7.16; N, 9.63. Found: C, 65.93; H, 7.05; N, 9.43.

EXAMPLE 50

N-[(4-Fluorophenyl)[1-[(methylamino)carbonyl]-4-piperidinyl]methyl]-N'-methyl-N-(2-phenylethyl)urea A solution of 2.25 g (0.0072 mol) of α-(4-fluorophenyl)-N-(2-phenylethyl)-4-piperidinemethanamine and 2.50 g (0.044 mol) of methyl isocyanate in 200 mL of methylene chloride was stirred at room temperature overnight. The solvent was removed in vacuo to give a solid. This was triturated with anhydrous ether, and the solid was collected to give 2.43 g (79.1%) of white solid, mp 186°-188° C.

Analysis calculated for: $C_{24}H_{31}N_4O_2F$: C, 67.58; H, 7.33; N, 13.14. Found: C, 67.45; H, 7.45; N, 12.97.

EXAMPLE 51

Following the procedure of Example 4 and using aniline and
a. 4-benzoyl-1-(2-naphthalenylmethyl)piperidine
b. 1-(2-naphthalenylmethyl)-4-(4-trifluoromethylbenzoyl)piperidine
c. 4-(4-methoxybenzoyl)-1-(2-naphthalenylmethyl)piperidine
d. 4-(4-fluorobenzoyl)-1-(2-naphthalenylmethyl)piperidine
there are obtained respectively
a. 1-(2-naphthalenylmethyl)-N,α-diphenyl-4-piperidinemethanamine
b. 1-(2-naphthalenylmethyl)-N-phenyl-α-[4-(trifluoromethyl)phenyl]-4-piperidinemethanamine
c. α-(4-methoxyphenyl)-1-(2-naphthalenylmethyl)-N-phenyl-4-piperidinemethanamine
d. α-(4-fluorophenyl)-1-(2-naphthalenylmethyl)-N-phenyl-4-piperidinemethanamine.

EXAMPLE 52

α-(4-Fluorophenyl)-N-(2-pyridinyl)-1-(3-phenoxypropyl)-4-piperidinemethanamine

Following the procedure of Example 4, the title compound is obtained from 2-aminopyridine and 4-(4-fluorobenzoyl)-1-(3-phenoxypropyl)piperidine.

EXAMPLE 53

4-[(4-Fluorophenyl)[(4-fluorophenyl)amino]methyl]-1-piperidinecarboximidamide

N,α-bis(4-fluorophenyl)-4-piperidinemethanamine and S-methylisothiouronium sulfate are reacted together according to the procedure of J. Amer. Chem. Soc. 71, 2476 (1949) to obtain the title compound.

EXAMPLE 54

1-(3-Chloropropyl)-N,α-bis(4-fluorophenyl)-4-piperidinemethanamine

Following the procedure of Example 2, the title compound is obtained from 3-bromo-1-chloropropane and N,α-bis(4-fluorophenyl)-4-piperidinemethylamine.

EXAMPLE 55

N-[3-[4-[(4-Fluorophenyl)[(4-fluorophenyl)amino]methyl]-1-piperidinyl]propyl]-2-pyrimidinamine A mixture of equivalent amounts of 1-(3-chloropropyl)-N,α-bis(4-fluorophenyl)-4-piperidinemethanamine, 2-aminopyrimidine, and sodium bicarbonate in 1-butanol is heated at reflux temperature until the reaction is complete. The solvent is removed and the residual material partitioned between water and methylene chloride. The methylene chloride layer is dried and concentrated to obtain the title compound.

EXAMPLE 56

N,α-bis(4-Fluorophenyl)-1-[3-(phenylamino)propyl]-4-piperidinemethanamine 1-(3-Chloropropyl)-N,α-bis(4-fluorophenyl)-4-piperidinemethanamine and excess aniline are heated together until the reaction is complete. Excess aniline is distilled off and the residual material partitioned between dilute aqueous sodium hydroxide and methylene chloride. The methylene chloride solution is dried and concentrated to obtain the title compound.

EXAMPLE 57

N,α-bis(4-Fluorophenyl)-1-[3-(4-phenyl-1-piperazinyl)propyl]-4-piperidinemethanamine Following the procedure of Example 55 and substituting 1-phenylpiperazine for 2-aminopyrimidine, the title compound is obtained.

EXAMPLE 58

2-[3-[4-[(4-Fluorophenyl)[(4-fluorophenyl)amino]methyl]-1-piperidinyl]propyl]-1H-isoindole-1,3-(2H)dione Following the procedure of Example 2, the title compound is obtained from N,α-bis(4-fluorophenyl)-4-piperidinemethanamine and N-(3-bromopropyl)phthalimide.

EXAMPLE 59

4-[(4-Fluorophenyl)[(4-fluorophenyl)amino]methyl]-1-piperidinepropanamine

Equimolar amounts of N,α-bis(4-fluorophenyl)-1-(3-phthalimido)propyl-4-piperidinemethanamine and 85% hydrazine hydrate are heated together in absolute ethanol until the reaction is complete. The mixture is cooled, diluted with water, acidified, filtered, concentrated, and the residue partitioned between dilute aqueous sodium hydroxide and methylene chloride. The methylene chloride solution is dried and concentrated to obtain the title compound.

EXAMPLE 60

N-[3-[4-[(4-Fluorophenyl)[(4-fluorophenyl)amino]methyl]-1-piperidinyl]propyl]-N'-methylurea The compound of Example 59 is reacted with methyl isocyanate in an aprotic solvent to obtain the title compound.

EXAMPLE 61

N-[3-[4-[(4-Fluorophenyl)[(4-fluorophenyl)amino]methyl]-1-piperidinyl]propyl]-N'-phenylurea The compound of Example 59 is reacted with phenyl isocyanate in an aprotic solvent to obtain the title compound.

EXAMPLE 62

Following the procedure of Example 2, and substituting for 3-chloro-1-(4-acetyl-2-methoxyphenoxy)propane
a. cyclopropylmethylbromide
b. 1-iodo-2,2,2-trifluoroethane
c. 2-bromoethanol d. 4-bromo-2-methyl-2-butene
e. 3-bromopropene
f. 6-(2-chloroethyl)-7-methyl-5H-thiazolo[3,2-a]pyrimidine-5-one (EP 0110435)
g. 1-benzyl-3-chloroethylimidozolidin-2-one (Neth. Appl. 6,410,202; CA 63 11572b)

there is correspondingly obtained a. 1-(cyclopropylmethyl)-N,α-bis(4-fluorophenyl)-4-piperidinemethanamine
b. N,α-bis(4-fluorophenyl)-1-(2,2,2-trifluoroethyl)-4-piperidinemethanamine
c. 4-[(4-fluorophenyl)[(4-fluorophenyl)amino]methyl]-1-piperidineethanol
d. N,α-bis(4-fluorophenyl)-1-(3-methyl-2-butenyl)-4-piperidinemethanamine
e. N,α-bis(4-fluorophenyl)-1-(2-propenyl)-4-piperidinemethanamine
f. 6-[2-[4-[(4-fluorophenyl)[(4-fluorophenyl)amino]methyl]-1-piperidinyl]ethyl]-7-methyl-5H-thiazolo[3,2-a]pyrimidin-5-one
g. 1-[2-[4-[(4-fluorophenyl)[(4-fluorophenyl)amino]methyl]-1-piperidinyl]ethyl-3-(phenylmethyl)-2,3-dihydro-1H-benzimidazol-2-one.

EXAMPLE 63

4-[[4-(3,4-Difluorophenyl)amino](4-fluorophenyl)methyl]-1-piperidinyl]-1-(4-fluorophenyl)-1-butanone Following the procedure of Example 2, the title compound is prepared by first reacting 2-(3-chloropropyl)-2-(4-fluorophenyl)-1,3-dioxolane with N-(3,4-difluorophenyl)-α-(4-fluorophenyl)-4-piperidinemethanamine followed by hydrolysis of the ethyleneglycol ketal with dilute acid.

EXAMPLE 64

4-[[(3,4-Difluorophenyl)amino](4-fluorophenyl)methyl]-α-(4-fluorophenyl)-1-piperidinebutanol The compound of Example 63 is reduced with sodium borohydride by procedures known to those skilled in the art to obtain the title compound.

EXAMPLE 65

1-[3-[(4-Chlorophenyl)thio]propyl]-N-(3,4-difluorophenyl)-α-(4-fluorophenyl)-4-piperidinemethanamine Following the procedure of Example 2, the title compound is prepared from 1-chloro-4-[(3-chloropropyl)thio]benzene [J. Amer. Chem. Soc. 82, 2505 (1960)] and N-(3,4-dichlorophenyl)-α-(4-fluorophenyl)-4-piperidinemethanamine.

EXAMPLE 66

1-[3-[(4-Chlorophenyl)sulfinyl]propyl]-N-(3,4-difluorophenyl)-α-(4-fluorophenyl)-4-piperidinemethanamine Following the procedure of Example 2, the title compound is prepared from 1-chloro-4-[(3-chloropropyl)sulfinyl]benzene and N-(3,4-difluorophenyl)-α-(4-fluorophenyl)-4-piperidinemethanamine.

EXAMPLE 67

1-[3-[(4-Chlorophenyl)sulfonyl]propyl]-N-(3,4-difluorophenyl)-α-(4-fluorophenyl)-4-piperidinemethanamine Following the procedure of Example 2, the title compound is prepared from 1-chloro-4-[(3-chloropropyl)sulfonyl]benzene and N-(3,4-difluorophenyl)-α-(4-fluorophenyl)-4-piperidinemethanamine.

EXAMPLE 68

Following the procedure of Example 35 and substituting for 2-(2-bromoethoxy)naphthalene,
a. 4-(3-chloropropyloxy)benzoic acid 1-methylethyl ester
b. 2-(2-bromoethyl)naphthalene there is obtained respectively
a. 4-[3-[4-[[(3,4-difluorophenyl)amino](4-fluorophenyl)methyl]-1-piperidinyl]propoxy]benzoic acid 1-methylethyl ester
b. N-(3,4-difluorophenyl)-α-(4-fluorophenyl)-1-[2-(2-naphthylenyl)ethyl]-4-piperidinemethanamine.

EXAMPLE 69

N,α-bis(3,4-Difluorophenyl)-1-(2-naphthalenylmethyl)-4-piperidinemethanamine

Following the procedure of Example 4, the title compound is obtained from 4-(3,4-difluorobenzoyl)-1-(2-naphthalenylmethyl)-4-piperidinemethanamine and 3,4-difluoroaniline.

EXAMPLE 70

α-(3,4-Difluorophenyl)-N-(4-fluorophenyl)-1-(2-naphthalenylmethyl)-4-piperidinemethanamine Following the procedure of Example 4, the title compound is obtained from 4-(3,4-difluorobenzoyl)-1-(2-naphthalenylmethyl)-4-piperidinemethanamine and 4-fluoroaniline.

EXAMPLE 71

N-[(4-Fluorophenyl)[1-(3-phenoxypropyl)-4-piperidinyl]methyl]-2-pyrimidinamine

α-(4-Fluorophenyl)-1-(3-phenoxypropyl)-4-piperidinemethanamine and 2-chloropyrimidine (equimolar quantities) are heated together in tetrahydrofuran at reflux temperature until the reaction is judged complete. The reaction mixture is concentrated and the residual material is partitioned between 1N NaOH solution and methylene chloride. The methylene chloride layer is dried and concentrated to obtain the title compound.

EXAMPLE 72

Following the procedure of Example 4, there is obtained from (4-fluorophenyl)[1-(2-naphthalenylmethyl)-4-piperidinyl]methanone and
a. 4-methoxyaniline
b. 4-chloroaniline
c. 2,4-difluoroaniline
d. 4-trifluoromethylaniline the following compounds respectively:
a. α-(4-fluorophenyl)-N-(4-methoxyphenyl)-1-(2-naphthalenylmethyl)-4-piperidinemethanamine
b. N-(4-chlorophenyl)-α-(4-fluorophenyl)-1-(2-naphthalenylmethyl)-4-piperidinemethanamine
c. N-(2,4-difluorophenyl)-α-(4-fluorophenyl)-1-(2-naphthalenylmethyl)-4-piperidinemethanamine
d. α-(4-fluorophenyl)-1-(2-naphthalenylmenthyl)-N-(4-trifluoromethylphenyl)-4-piperidinemethanamine.

EXAMPLE 73

Following the procedure of Example 4 and substituting for 4-(4-fluorophenyl)[1-(1-methylethyl)-4-piperidinyl]methanone hydrochloride the following:

a. 1-(3-phenoxypropyl)-3-(3-trifluoromethylbenzoyl)-pyrrolidine
b. 3-(4-fluorobenzoyl)-1-(2-naphthalenylmethyl)azetidine
c. 2-(4-fluorobenzoyl)-1-(3-phenoxypropyl)azetidine
d. 1-benzyl-3-(4-fluorobenzoyl)pyrrolidine
e. 1-benzyl-3-(3-trifluoromethylbenzoyl)pyrrolidine
f. 1-(2-ethoxyethyl)-3-(4-fluorobenzoyl)pyrrolidine
there are obtained respectively:
a. N-(4-fluorophenyl)-1-(3-phenoxypropyl)-α-(3-trifluoromethoxyphenyl)-3-pyrrolidinemethanamine
b. N,α-bis(4-fluorophenyl)-1-(2-naphthalenylmethyl)-3-azetidinemethanamine
c. N,α-bis(4-fluorophenyl)-1-(3-phenoxypropyl)-2-azetidinemethanamine
d. 1-benzyl-N,α-bis(4-fluorophenyl)-3-pyrrolidinemethanamine
e. 1-benzyl-N-(4-fluorophenyl)-α-(3-trifluoromethylphenyl)-3-pyrrolidinemethanamine
f. 1-(2-ethoxyethyl)-N,α-bis(4-fluorophenyl)-3-pyrrolidinemethanamine.

EXAMPLE 74

Following the procedure of Example 4 and substituting for 4-(4-fluorophenyl)[1-(1-methylethyl)-4-piperidinyl]methanone hydrochloride the following:
a. 2-(4-fluorobenzoyl)-1-(3-phenoxypropyl)pyrrolidine
b. 2-(4-fluorobenzoyl)-1-(3-phenoxypropyl)piperidine
there are obtained respectively:
a. N,α-bis(4-fluorophenyl)-1-(3-phenoxypropyl)-2-pyrrolidinemethanamine
b. N,α-bis(4-fluorophenyl)-1-(3-phenoxypropyl)-2-piperidinemethanamine.

EXAMPLE 75

N-[3-[4-[(4-Fluorophenyl)[4-fluorophenyl)amino]methyl]-1-piperidinyl]propyl]guanidine The compound of Example 59 and S-methylisothiouronium sulfate are reacted together according to the procedure of J. Amer. Chem. Soc. 71, 2476 (1979) to obtain the title compound.

EXAMPLE 76

α-(3,4-dichlorophenyl)-N-(4-fluorophenyl)-4-piperidinemethanamine

The title compound is obtained following the procedure of Example 31 and using 4-(3,4-dichlorobenzoyl)-piperidine hydrochloride and 4-fluoroaniline.

EXAMPLE 77

Following the procedure of Example 2 and using α-(3,4-dichlorophenyl)-N-(4-fluorophenyl)-4-piperidinemethanamine and the following:
a. 3-chloropropyloxybenzene
b. 2-bromomethylnaphthalene
there are obtained respectively:
a. α-(3,4-dichlorophenyl)-N-(4-fluorophenyl)-1-(3-phenoxypropyl)-4-piperidinemethanamine
b. α-(3,4-dichlorophenyl)-N-(4-fluorophenyl)-1-(2-naphthylenylmethyl)-4-piperidinemethanamine.

EXAMPLE 78

N-(4-Fluorophenyl)-α-phenyl-3-piperidinemethanamine

The title compound is obtained from 4-fluoroaniline and 3-benzoylpiperidine hydrochloride using the procedure of Example 31.

EXAMPLE 79

1-[4-[3-[3-[[(4-Fluorophenyl)amino]phenylmethyl]-1-piperidinyl]propoxy]-3-methoxyphenyl]ethanone Following the procedure of Example 2, the title compound is obtained where N-(4-fluorophenyl)-α-phenyl-3-piperidinemethanamine is substituted for N,α-bis(4-fluorophenyl)-4-piperidinemethanamine.

EXAMPLE 80

N-(3,4-Difluorophenyl)-α-(4-fluorophenyl)-1-[3-(2-naphthalenyloxy)propyl]-4-piperidinemethanamine dihydrochloride A mixture of 4-[[(3,4-difluorophenyl)amino](4-fluorophenyl)methyl]piperidine (4.70 g, 0.0147 mol), 2-(3-chloropropyloxy)naphthalene) (3.23 g, 0.0147 mol), and sodium bicarbonate (5.53 g, 0.0658 mol) in 350 mL of 1-butanol containing sodium iodide was heated at reflux for 24 h. The butanol was removed by rotary evaporator and the residue partitioned between chloroform and water. The chloroform layer was washed with 5% sodium hydroxide, dried (Na$_2$SO$_4$) and filtered. Chloroform was removed to give a brown oil. This oil was dissolved in methylene chloride and placed on a 300 g silica gel column for flash chromatography. Elution was accomplshed using methylene chloride, 1% methanol-methylene chloride, and 2% methanol-methylene chloride. Fractions of similar purity were combined and solvents removed to give a dark brown oil. This material was converted to the HCl salt and recrystallized from methanol-diethyl ether. A white solid was isolated and dried 16 h in vacuo at 80° C. This procedure produced 5.08 g (59.8%) of white crystalline solid, mp 225°-226° C.

Analysis calculated for: C$_{31}$H$_{31}$N$_2$OF$_3$.2HCl: C, 64.47; H, 5.76; N, 4.85. Found: C, 64.53; H, 5.89; N, 4.80.

EXAMPLE 81

N-(3,4-Difluorophenyl)-α-(4-fluorophenyl)-1-[2-(1-naphthalenyloxy)ethyl]-4-piperidinemethanamine dihydrochloride A mixture of 4-[[(3,4-difluorophenyl)amino](4-fluorophenyl)methyl]piperidine (5.41 g, 0.0169 mol), 1-(2-bromoethoxy)naphthalene (4.23 g, 0.0169 mol) and sodium bicarbonate (5.53 g, 0.059 mol) in 350 mL of 1-butanol containing sodium iodide (0.2 g) was heated 20 h at reflux. The reaction was concentrated to dryness and partitioned between chloroform and water. The chloroform layer was washed with 5% sodium hydroxide and dried (Na$_2$SO$_4$). Chloroform was removed to give a brown oil. The oil was dissolved in methylene chloride and placed on a silica gel column for flash chromatography. Elution was accomplished using 1% methanol-methylene chloride and 2% methanol-methylene chloride. Fractions of similar purity were combined and solvents removed to give a fluffy grey material. This material was converted to the HCl salt and the salt was recrystallized from methanol-diethyl ether to give a whitish-grey solid. The material was dried 16 h in vacuo at 80° C. This process provided 5.06 g (53.1%) of greyish material, mp 212°–215° C. (dec).

Analysis calculated for: $C_{30}H_{29}N_2OF_3 \cdot 2HCl$: C, 63.95; H, 5.54; N, 4.97. Found: C, 63.78; H, 5.63; N, 4.95.

EXAMPLE 82

N-(3,4-Difluorophenyl)-α-(4-fluorophenyl)-1-(2-phenoxyethyl)-4-piperidinemethanamine dihydrochloride A mixture of N-(3,4-difluorophenyl)-α-(4-fluorophenyl)-4-piperidinemethanamine (5.45 g, 0.0170 mol), 2-bromoethylphenyl ether (3.42 g, 0.0170 mol) and sodium bicarbonate (5.53 g, 0.0658 mol) in 1-butanol (350 mL) containing sodium iodide (0.2 g) was heated 16 h at reflux. The solvent was removed and the residue partitioned between water and chlorform. The chloroform layer was washed with water and 5% sodium hydroxide. The chloroform was dried ($Na_2SO_4$), filtered and the chloroform was removed to give a brown oil. This material was subjected to flash chromatography on silica gel. Elution was accomplished using 1% methanol-methylene chloride and 2% methanol-methylene chloride. Fractions of similar purity were combined and solvents removed to give a brown oil. This material was converted to the hydrochloride salt and recrystallized from methanol-diethyl ether. A white solid was isolated and dried 16 h in vacuo at 80° C. This process provided 5.55 g (63.6%) of white crystalline solid, mp 211°–215° C.

Analysis calculated for: $C_{26}H_{27}F_3N_2O \cdot 2HCl$: C, 60.82; H, 5.69; N, 5.46. Found: C, 60.47; H, 5.77; N, 5.41.

EXAMPLE 83

N,α-bis(4-Fluorophenyl)-3-pyrrolidinemethanamine

The title compound is prepared from 4-fluoroaniline and 3-(4-fluorobenzoyl)pyrrolidine hydrochloride according to the procedure of Example 31.

EXAMPLE 84

N,α-bis(4-Fluorophenyl)-3-piperidinemethanamine

The title compound is prepared from 4-fluoroaniline and 3-(4-fluorobenzoyl)piperidine hydrochloride according to the procedure of Example 31.

EXAMPLE 85

N,α-bis(4-Fluorophenyl)-1-(3-phenoxypropyl)-3-pyrrolidinemethanamine

The title compound is prepared from N,α-bis(4-fluorophenyl)-3-pyrrolidinemethanamine hydrochloride and 3-phenoxypropylbromide according to the procedure of Example 8.

EXAMPLE 86

N,α-bis(4-Fluorophenyl)-1-(3-phenoxypropyl)-3-piperidinemethanamine

The title compound is prepared from N,α-bis(4-fluorophenyl)-3-pyrrolidinemethanamine hydrochloride and 3-phenoxypropyl bromide according to the procedure of Example 8.

EXAMPLE 87

Using the procedures of Example 8 and replacing 3-phenoxypropyl bromide with
a. 1-(2-chloroethyl)-3-methyl-2-imidazolidinone
b. 1-(2-chloroethyl)-3-butyl-2-imidazolidinone
c. 1-(2-chloroethyl)-2-imidazolidinone
d. 1-(3-chloropropyl)-2-imidazolidinone
e. 1-(2-chloroethyl)-2-benzimidazolidinone
there are obtained respectively
a. 1-[2-[4-[(4-fluorophenyl)[(4-fluorophenyl)amino]methyl]-1-piperidinyl]ethyl]-3-methyl-2-imidazolidinone
b. 1-[2-[4-[(4-fluorophenyl)[(4-fluorophenyl)amino]methyl]-1-piperidinyl]ethyl]-3-butyl-2-imidazolidinone
c. 1-[2-[4-[(4-fluorophenyl)[(4-fluorophenyl)amino]methyl]-1-piperidinyl]ethyl]-2-imidazolidinone
d. 1-[3-[4-[(4-fluorophenyl)[(4-fluorophenyl)amino]methyl]-1-piperidinyl]propyl]-2-imidazolidinone
e. 1-[2-[4-[(4-fluorophenyl)[(4-fluorophenyl)amino]methyl]-1-piperidinyl]ethyl]-1,3-dihydro-2H-benzimidazol-2-one.

EXAMPLE 88

N,α-bis(4-fluorophenyl)-N-methyl-1-(3-phenoxypropyl)-4-piperidinylmethanamine

The title compound is prepared from N,α-bis(4-fluorophenyl)-1-(3-phenoxypropyl)-4-piperidinemethanamine and methyl iodide by usual alkylation conditions known to those skilled in the art.

TABLE 1

| Ex. No. | (X)m | R | Ring Position | Ring Size | (Q)nAr | R' | Salt |
|---|---|---|---|---|---|---|---|
| 1 | 4-F | H | 4 | 6 | 4-FC6H4— | H | 0.5 H2O |
| 2 | 4-F | H | 4 | 6 | 4-FC6H4— | —(CH2)3O—C6H3(3-OCH3)(C(=O)CH3) | 0.5 H2O |
| 3 | 4-F | H | 4 | 6 | 4-FC6H4— | —CH2CH=CHC6H5 | C6H5CH=CHCH2⊕Cl⊖ |
| 4 | 4-F | H | 4 | 6 | 4-FC6H4— | CH(CH3)2 | 2 HCl.H2O |
| 5 | 4-F | H | 4 | 6 | 4-FC6H4— | —CH2CH=CHC6H5 | 2 HCl.H2O |
| 6 | 4-F | H | 4 | 6 | 4-FC6H4— | —CH2—CH(OH)CH2OC6H5 | 2 HCl.0.5 H2O |
| 7 | 4-F | H | 4 | 6 | 4-FC6H4— | —CH2—CH(OH)CH2OC6H5 (low melting diasteriomers) | 2 HCl.0.5 H2O |
| 8 | 4-F | H | 4 | 6 | 4-FC6H4— | —(CH2)3OC6H5 | 2 HCl.0.5 H2O |
| 9 | 4-F | H | 4 | 6 | 4-FC6H4— | —C(=O)NHCH3 | — |
| 10 | 4-F | H | 4 | 6 | 4-FC6H4— | —C(=O)NHC6H5 | — |
| 11 | 4-F | H | 4 | 6 | 4-FC6H4— | —(CH2)4OC6H5 | 2 HCl |
| 12 | 4-F | —C(=O)CH3 | 4 | 6 | 4-FC6H4— | —(CH2)3O—C6H3(3-OCH3)(C(=O)CH3) | oxalate.0.5 H2O |
| 13 | 4-F | H | 4 | 6 | 4-FC6H4— | —(CH2)3O—C6H4(C(CH3)3) | 0.5 H2O |

TABLE 1-continued
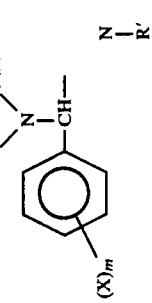
| Ex. No. | (X)m | R | Ring Position | Ring Size | (Q)nAr | R' | Salt |
|---|---|---|---|---|---|---|---|
| 14 | 4-F | H | 4 | 6 | 4-FC6H4— | —(CH2)3O—C(=O)—C6H4—C(CH3)3 | 0.5 H2O |
| 15 | 4-F | H | 4 | 6 | 4-FC6H4— | —CH2-naphthyl | — |
| 16 | 4-F | H | 4 | 6 | 4-FC6H4— | —C(=O)NHCH2CH2N(C2H5)2 | 0.5 H2O |
| 17 | 4-F | H | 4 | 6 | 4-FC6H4— | pyrimidinyl | — |
| 18 | 4-F | H | 4 | 6 | 4-FC6H4— | —CH2-quinolinyl | oxalate·0.5 H2O |
| 19 | 4-F | H | 4 | 6 | 4-FC6H4— | —C(=O)—C6H5 | — |
| 20 | 4-F | H | 4 | 6 | 4-FC6H4— | —CH2CH2O-naphthyl | 2 HCl |
| 21 | 4-F | H | 4 | 6 | 4-FC6H4— | H(+)isomer | 2.5 HCl |
| 22 | 4-F | H | 4 | 6 | 4-FC6H4— | H(−)isomer | 3 HCl |

TABLE 1-continued

| Ex. No. | (X)m | R | Ring Position | Ring Size | (Q)nAr | R' | Salt |
|---|---|---|---|---|---|---|---|
| 23 | 4-F | H | 4 | 6 | 4-FC6H4— | —CH2C6H5 | 2 HCl |
| 24 | 4-F | H | 4 | 6 | 4-FC6H4— | —(CH2)3O-C6H4-C(=O)-CH(CH3)2 | 2 HCl |
| 25 | 4-F | H | 4 | 6 | 4-FC6H4— | —CH2CH2N (quinazoline-2,4-dione-3-yl) | 2 HCl |
| 26 | 4-F | H | 4 | 6 | 4-FC6H4— | cyclohexyl | 2 HCl.0.5 H2O |
| 27 | 4-F | H | 4 | 6 | 4-FC6H4— | —CH2CH(CH3)2 | 2 HCl.0.5 H2O |
| 28 | 4-F | H | 4 | 6 | 4-FC6H4— | -propyl | 2 HCl.0.5 H2O |
| 29 | 4-F | H | 4 | 6 | 4-FC6H4— | —CH2CH2OC2H5 | 2 HCl.0.5 H2O |
| 30 | 4-F | H | 4 | 6 | 4-FC6H4— | H | — |
| 31 | 4-F | H | 4 | 6 | 3,4-diFC6H3 | H | 2 HCl.0.5 H2O |
| 32 | 4-F | H | 4 | 6 | 3,4-diFC6H3 | —(CH2)3OC6H5 | oxalate |
| 33 | 4-F | H | 4 | 6 | 3,4-diFC6H3 | —CH2-(quinoline) | oxalate.0.5 H2O |
| 34 | 4-F | H | 4 | 6 | 3,4-diFC6H3— | —CH2-(naphthalene) | 2 HCl |
| 35 | 4-F | H | 4 | 6 | 3,4-diFC6H3— | —CH2CH2O-(naphthalene) | 2 HCl |

TABLE 1-continued

| Ex. No. | (X)m | R | Ring Position | Ring Size | (Q)nAr | R' | Salt |
|---|---|---|---|---|---|---|---|
| 36 | 4-F | H | 4 | 6 | 4-FC$_6$H$_4$—CH$_2$ | H | 2 HCl.1.5 H$_2$O |
| 37 | 4-F | H | 4 | 6 | 4-FC$_6$H$_4$—CH$_2$ | —CH$_2$CH$_2$C$_6$H$_5$ | 1.5 fumarate |
| 38 | 4-F | CH$_3$C(O)— | 4 | 6 | 4-FC$_6$H$_4$—CH$_2$ | —CH$_2$CH$_2$C$_6$H$_5$ | fumarate |
| 39 | 4-F | CH$_3$NHC(O)— | 4 | 6 | 4-FC$_6$H$_4$—CH$_2$ | —CH$_2$CH$_2$C$_6$H$_5$ | 1.5 fumarate |
| 40 | 4-F | H | 4 | 6 | 4-FC$_6$H$_4$—CH$_2$ | —(CH$_2$)$_3$OC$_6$H$_5$ | 2 HCl.0.5 H$_2$O |
| 41 | 4-F | H | 4 | 6 | 4-FC$_6$H$_4$—CH$_2$ | —(CH$_2$)$_3$O-(3-CH$_3$O,4-CH$_3$C(O))C$_6$H$_3$ | 2 HCl.0.5 H$_2$O |
| 42 | 4-F | H | 4 | 6 | 4-FC$_6$H$_4$—CH$_2$ | —C(O)NHCH$_3$ | fumarate |
| 43 | 4-F | CH$_3$NHC(O)— | 4 | 6 | 4-FC$_6$H$_4$—CH$_2$ | —C(O)NHCH$_3$ | — |
| 44 | 4-F | CH$_3$C(O)— | 4 | 6 | 4-FC$_6$H$_4$—CH$_2$ | —(CH$_2$)$_3$OC$_6$H$_5$ | fumarate |
| 45 | 4-F | C$_6$H$_5$NHC(O)— | 4 | 6 | 4-FC$_6$H$_4$—CH$_2$ | —C(O)NHC$_6$H$_5$ | — |
| 46 | 4-F | H | 4 | 6 | C$_6$H$_5$—CH$_2$CH$_2$— | H | 2 fumarate.0.5 H$_2$O |
| 47 | 4-F | H | 4 | 6 | C$_6$H$_5$—CH$_2$CH$_2$— | —(CH$_2$)$_3$O-(3-CH$_3$O,4-CH$_3$C(O))C$_6$H$_3$ | 2 fumarate.H$_2$O |

TABLE 1-continued

| Ex. No. | (X)m | R | Ring Position | Ring Size | (Q)$_n$Ar | R' | Salt |
|---|---|---|---|---|---|---|---|
| 48 | 4-F | H | 4 | 6 | C$_6$H$_5$—CH$_2$CH$_2$— | —C(O)NHC$_6$H$_5$ | 0.75 fumarate·0.5 H$_2$O |
| 49 | 4-F | H | 4 | 6 | C$_6$H$_5$—CH$_2$CH$_2$— | —C(O)NHCH$_3$ | 0.5 fumarate·0.5 H$_2$O |
| 50 | 4-F | CH$_3$NHC(O)— | 4 | 6 | C$_6$H$_5$—CH$_2$CH$_2$— | —C(O)NHCH$_3$ | — |
| 51a | H | H | 4 | 6 | C$_6$H$_5$— | —CH$_2$-naphthyl | — |
| 51b | 4-CF$_3$— | H | 4 | 6 | C$_6$H$_5$— | —CH$_2$-naphthyl | — |
| 51c | 4-CH$_3$O— | H | 4 | 6 | C$_6$H$_5$— | —CH$_2$-naphthyl | — |
| 51d | 4-F | H | 4 | 6 | C$_6$H$_5$— | —CH$_2$-naphthyl | — |
| 52 | 4-F | H | 4 | 6 | 2-pyridyl | —(CH$_2$)$_3$—O—C$_6$H$_5$ | — |
| 53 | 4-F | H | 4 | 6 | 4FC$_6$H$_4$— | —C(=NH)—NH$_2$ | — |
| 54 | 4-F | H | 4 | 6 | 4FC$_6$H$_4$— | —(CH$_2$)$_3$Cl | — |

TABLE 1-continued
| Ex. No. | (X)m | R | Ring Position | Ring Size | (Q)ₙAr | R' | Salt |
|---|---|---|---|---|---|---|---|
| 55 | 4-F | H | 4 | 6 | 4-FC₆H₄— | 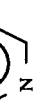—(CH₂)₃NH | — |
| 56 | 4-F | H | 4 | 6 | 4-FC₆H₄— | —(CH₂)₃NHC₆H₅ | — |
| 57 | 4-F | H | 4 | 6 | 4-FC₆H₄— | —(CH₂)₃N | — |
| 58 | 4-F | H | 4 | 6 | 4-FC₆H₄— | 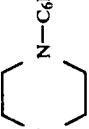—(CH₂)₃ | — |
| 59 | 4-F | H | 4 | 6 | 4-FC₆H₄— | —(CH₂)₃NH₂ | — |
| 60 | 4-F | H | 4 | 6 | 4-FC₆H₄— | 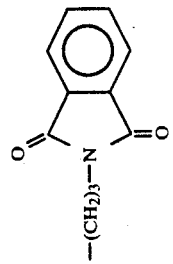—(CH₂)₃NHCNHCH₃ | — |
| 61 | 4-F | H | 4 | 6 | 4-FC₆H₄— | —(CH₂)₃NHCNHC₆H₅ | — |
| 62a | 4-F | H | 4 | 6 | 4-FC₆H₄— | —CH₂ | — |
| 62b | 4-F | H | 4 | 6 | 4-FC₆H₄— | —CH₂CF₃ | — |
| 62c | 4-F | H | 4 | 6 | 4-FC₆H₄— | —CH₂CH₂OH | — |
| 62d | 4-F | H | 4 | 6 | 4-FC₆H₄— | —CH₂CH=C(CH₃)₂ | — |
| 62e | 4-F | H | 4 | 6 | 4-FC₆H₄— | CH₂CH=CH₂ | — |

TABLE 1-continued

| Ex. No. | (X)m | R | Ring Position | Ring Size | (Q)ₙAr | R' | Salt |
|---|---|---|---|---|---|---|---|
| 62f | 4-F | H | 4 | 6 | 4-FC₆H₄— | —CH₂CH₂—[thiazolopyrimidinone with CH₃] | — |
| 62g | 4-F | H | 4 | 6 | 4-FC₆H₄— | —CH₂CH₂—[benzimidazolone with N—CH₂C₆H₅] | — |
| 63 | 4-F | H | 4 | 6 | 3,4-diFC₆H₃ | —(CH₂)₃—C(=O)—C₆H₄-4-F | — |
| 64 | 4-F | H | 4 | 6 | 3,4-diFC₆H₃ | —(CH₂)₃—CH(OH)—C₆H₄-4-F | — |
| 65 | 4-F | H | 4 | 6 | 3,4-diFC₆H₃ | —(CH₂)₃—S—C₆H₄-4-Cl | — |
| 66 | 4-F | H | 4 | 6 | 3,4-diFC₆H₃ | —(CH₂)₃—S(=O)—C₆H₄-4-Cl | — |

TABLE 1-continued

Structure: R-N(CH(Ar-(X)m))-(Q)n-Ar with N-R'

| Ex. No. | (X)m | R | Ring Position | Ring Size | (Q)nAr | R' | Salt |
|---|---|---|---|---|---|---|---|
| 67 | 4-F | H | 4 | 6 | 3,4-diFC$_6$H$_3$ | —(CH$_2$)$_3$—S(=O)$_2$—C$_6$H$_4$Cl | — |
| 68a | 4-F | H | 4 | 6 | 3,4-diFC$_6$H$_3$ | —(CH$_2$)$_3$—O—C$_6$H$_4$—CO—CH(CH$_3$)$_2$ | — |
| 68b | 4-F | H | 4 | 6 | 3,4-diFC$_6$H$_3$ | —CH$_2$CH$_2$-naphthyl | — |
| 69 | 3,4-diF | H | 4 | 6 | 3,4-diFC$_6$H$_3$ | —CH$_2$-naphthyl | — |
| 70 | 3,4-diF | H | 4 | 6 | 4-FC$_6$H$_4$ | —CH$_2$-naphthyl | — |
| 71 | 4-F | H | 4 | 6 | 2-pyrimidinyl | —(CH$_2$)$_3$OC$_6$H$_5$ | — |
| 72a | 4-F | H | 4 | 6 | 4-CH$_3$OC$_6$H$_4$— | —CH$_2$-naphthyl | — |

TABLE 1-continued

| Ex. No. | (X)m | R | Ring Position | Ring Size | (Q)nAr | R' | Salt |
|---|---|---|---|---|---|---|---|
| 72b | 4-F | H | 4 | 6 | 4-ClC₆H₄— | —CH₂-naphthyl | — |
| 72c | 4-F | H | 4 | 6 | 3,4-diFC₆H₄— | —CH₂-naphthyl | — |
| 72d | 4-F | H | 4 | 6 | 4-CF₃C₆H₄— | —CH₂-naphthyl | — |
| 73a | 3-CF₃ | H | 3 | 5 | 4-FC₆H₄— | —(CH₂)₃OC₆H₅ | — |
| 73b | 4-F | H | 3 | 4 | 4-FC₆H₄— | —(CH₂)₃OC₆H₅ | — |
| 73c | 4-F | H | 2 | 4 | 4-FC₆H₄— | —(CH₂)₃OC₆H₅ | — |
| 73d | 4-F | H | 3 | 4 | 4-FC₆H₄— | —CH₂C₆H₅ | — |
| 73e | 3-CF₃ | H | 3 | 5 | 4-FC₆H₄— | CH₂C₆H₅ | — |
| 73f | 4-F | H | 3 | 5 | 4-FC₆H₄— | CH₂CH₂OC₂H₅ | — |
| 74a | 4-F | H | 2 | 5 | 4-FC₆H₄— | —(CH₂)₃OC₆H₅ | — |
| 74b | 4-F | H | 2 | 6 | 4-FC₆H₄— | —(CH₂)₃OC₆H₅ | — |
| 75 | 4-F | H | 4 | 6 | 4-FC₆H₄— | —(CH₂)₃NHCNH₂ (=NH) | — |
| 76a | 3,4-diCl | H | 4 | 6 | 4-FC₆H₄— | H | — |
| 77a | 3,4-diCl | H | 4 | 6 | 4-FC₆H₄— | —(CH₂)₃OC₆H₅ | — |
| 77b | 3,4-diCl | H | 4 | 6 | 4-FC₆H₄— | —CH₂-naphthyl | — |
| 78 | H | H | 3 | 6 | 4-FC₆H₄— | H | — |

TABLE 1-continued

[Structure: R-N(-(Q)n-Ar)-CH(-C6H4(X)m)-N(R')]

| Ex. No. | (X)m | R | Ring Position | Ring Size | (Q)nAr | R' | Salt |
|---|---|---|---|---|---|---|---|
| 79 | H | H | 3 | 6 | 4-FC6H4— | —(CH2)3O—C6H3(OCH3)(OCCH3=O) | — |
| 80 | 4-F | H | 4 | 6 | 3,4-diFC6H3— | —(CH2)3—O-naphthyl | 2 HCl |
| 81 | 4-F | H | 4 | 6 | 3,4-diFC6H3— | —CH2CH2O-naphthyl | 2 HCl |
| 82 | 4-F | H | 4 | 6 | 3,4-diFC6H3— | —(CH2)2OC6H5 | 2 HCl |
| 83 | 4-F | H | 3 | 5 | 4-FC6H5— | H | — |
| 84 | 4-F | H | 3 | 6 | 4-FC6H4— | H | — |
| 85 | 4-F | H | 3 | 5 | 4-FC6H4— | —(CH2)3OC6H5 | — |
| 86 | 4-F | H | 3 | 6 | 4-FC6H4— | —(CH2)3OC6H5 | — |
| 87a | 4-F | H | 4 | 6 | 4-FC6H4— | —(CH2)2—N(C=O)(NCH3) | — |
| 87b | 4-F | H | 4 | 6 | 4-FC6H4— | —(CH2)2—N(C=O)(NC4H9) | — |

TABLE 1-continued
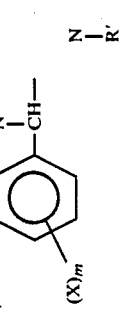
| Ex. No. | (X)m | R | Ring Position | Ring Size | (Q)nAr | R' | Salt |
|---|---|---|---|---|---|---|---|
| 87c | 4-F | H | 4 | 6 | 4-FC6H4— | —(CH2)2—N(C=O)(CH2)3NH (5-membered lactam) | — |
| 87d | 4-F | H | 4 | 6 | 4-FC6H4— | —(CH2)3—N(C=O)(CH2)3NH (5-membered lactam) | — |
| 87e | 4-F | H | 4 | 6 | 4-FC6H4— | —(CH2)2—N(C=O)-benzo-NH | — |
| 88 | 4-F | CH3 | 4 | 6 | 4-FC6H4— | —(CH2)3OC6H5 | — |

PHARMACOLOGICAL METHODS

Screening Method for Calcium Channel Blocking Activity in Isolated Rabbit Aorta Spiral strips of thoracic aorta are obtained from non-fasted New Zealand white rabbits killed by cervical dislocation. The aortic strips are prepared by the method of Furchgott, R. F. and Bhadrakom, S. (1953) J. Pharmacol. Exp. Ther. 108:129–143 and suspended in a modified Krebs solution aerated with a mixture of 95% oxygen and 5% carbon dioxide. Measurements of tissue isometric contractions are made with Grass force-displacement transducers (FT03C). Experiments were conducted according to the method of Godfraind, T. and Kaba, A. (1969) Br. J. Pharmacol. 6:549–560. Briefly, the strips were sequentially bathed in a modified Krebs solution containing calcium chloride, 2.6 mM; a calcium-free modified Krebs buffer: and then in a depolarizing calcium-free buffer containing 100 nM potassium chloride. Cumulative addition of calcium chloride to the last buffer induces isometric contractions of the tissue, which are measured and recorded on a Grass polygraph (Model 7). Contractile responses induced by calcium chloride are conducted in the absence and then followed by the presence of the test compound and then are compared. Responses of at least three aortic strips are used to calculate $Pa_2$ values according to the method of Van Rossum, J. M. (1963) Arch. Int. Pharmacodyn. 143:299–330.

In this test the more active compounds such as those of Examples 2, 6, and 14 had $pA_2$ values of 8.80, 7.99, and 8.49 respectively as compared to the reference compound verapamil ($Pa_2 = 8.0$).

Test Method for Antihypertensive Effect of Orally Administered Drugs to Unanesthetized Spontaneously Hypertensive Rats At least 24 hours prior to compound administration, adult male spontaneously hypertensive rats (SHR) are anesthetized with sodium pentobarbital (50 mg/kg IP). A polyethylene catheter (PE-50) is implanted in a carotid artery or the abdominal aorta for the direct measurement of arterial blood pressure. The catheter is exteriorized at the nape of the neck and connected through a swivel device to a Statham P23(Id) pressure transducer. Blood pressure is displayed on a Grass polygraph (Model 7) and simultaneously digitized and collected with a Buxco Electronics Datalogger. Data are obtained from conscious, freely moving rats that are allowed free access to food and water. After obtaining baseline blood pressure data for 1–1.5 hours, compounds are administered orally as solutions or as uniform suspensions (30 mg/kg in 5 mL/kg of 0.5 Tween 80 in distilled water or other suitable vehicle as necessary). Blood pressure are measured at 0.5, 1, 1.5, 2, 3, 4, 5, 6, and 24 hours after dosing. The mean arterial blood pressure (MABP) values obtained at these intervals are used to calculate an average percent change from pre-dose MABP for the 0.5–2.0 hour, 3–6 hour, and 24 hour periods. Raw blood pressure are analyzed by a paired, one-tailed t-test. Decreases in MABP are considered statistically significant when <0.05.

The more active compounds such as those of Examples 20 and 35 are effective in lowering blood pressure in the spontaneously hypertensive rats.

Procedure for Determinating Effect of Compounds on Coronary Blood Flow

The procedure used to determine the effect of the aforementioned compounds on coronary arterial blood flow is described as follows.

Mongrel dogs of either sex were anesthetized with phenobarbital sodium (100 mg/kg) and pentobarbital sodium (100 mg total dose). The trachea was surgically exposed, a tracheal tube was inserted and the dog was artificially respired with room air using a Harvard Model 613 Respirator. The heart was exposed by a left thoracotomy at the fourth intercostal space. An approximately 1.5 cm segment of the left arterior descending coronary artery was exposed and a Statham electromagnetic blood flow probe was implanted around the vessel. The flow probe was implanted around the vessel. The flow probe cable was connected to a Statham Model 2201 Blood Flow Meter. Continuous recordings of carotid arterial blood pressure, and a coronary arterial blood flows, were obtained using a Grass Model 5 Polygraph.

The compounds were administered via a femoral vein. Changes in both magnitude and duration of change in coronary blood flow from pre-drug levels were determined. Generally, multiple doses of the compounds tested were administered to a single dog. Appropriate intervals between doses were allowed to permit the blood flow to return to control levels.

Illustratively, the compounds of Examples 20 and 35 showed an increase in coronary arterial blood flow of about 75–120 mL/min at 1 mg/kg IV.

Pharmaceutical Compositions and Administration

Compositions for administration to living animals are comprised of at least one of the compounds of Formula I according to the methods of treatment of the invention in association with a pharmaceutical carrier or excipient. Effective quantities of the compounds may be administered in any one of various ways, for example, orally as in elixirs, capsules, tablets or coated tablets, parenterally in the form of sterile solutions suspensions and in some cases intravenously in the form of sterile solutions, intranasally and to the throat or bronchial region in the form of drops, gargles, syrups, powders, etc. or subcutaneously. Suitable tableting excipients include lactose, potato and maize starches, talc, gelatin, stearic, and silicic acids, magnesium stearate and polyvinyl pyrrolidone.

For the parenteral administration, the carrier or excipient can be comprised of a sterile parenterally acceptable liquid, e.g., water or arachis oil contained in ampoules.

Advantageously, the compositoins are formulated as dosage units, each unit being adapted to supply a fixed dose of active ingredients. Tablets, coated tablets, capsules, ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the following guide to projected human oral dosages is derived by knowledge of the activity obtained in animal screening tests for the various indications in the methods of the invention compared to activity of known agents in the field in the same animal screening tests. However, the amount of the active compounds administered need not be limited by these comparisons due to uncertainty in transposing comparative animal data to human treatments.

Oral dosages projected for hypertension for an adult human of the order of 40–300 mg/day divided into 2 or 3 doses. Thus, for example, two capsules each containing 10–50 mg active agent of Formula I could be administered 2-3 times daily for blood pressure lowering.

Oral dosages projected for use in the treatment of angina for an adult human are of the order of 60–400 mg/day divided into 2 or 3 doses. Thus, for example, two capsules each containing 10–30 mg active agent of Formula I could be administered 2-5 daily to increase coronary blood flow.

Other routes of administration such as subcutaneous, intraperitoneal, intravenous, etc. are possible with dosage forms being adapted to the situation as will be obvious to one skilled in the art of medicine.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed:

1. Compounds having the formula

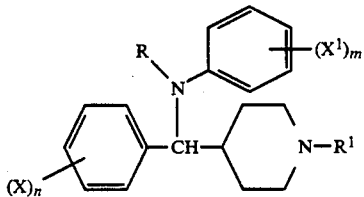

wherein
R is selected from H, loweralkyl, R²C(O)—R²OC(O)—, R²NHC(O)—, or (R²)²NC(O)—;
m=0–2;
X and X' are independently selected from halogen, loweralkyl, trifluoromethyl, or —OR²;
R¹ is selected from hydrogen, loweralkyl, loweralkylene, cycloloweralkyl, loweralkylcycloloweralkyl, CF₃CH₂—, or -(alk)p—Y where p is 0 or 1, alk refers to hydrocarbon radical, straight or branched, of from one to six carbons and may include one or more double bonds, and Y is —C(O)NHR₂, —C(NH)NH₂, phenyl, naphthyl, hydroxy, loweralkoxy, loweralkyleneoxy, aryloxy (where aryl is phenyl, naphthyl, 2-methoxy-4-acetylphenyl, 4-loweralkylcarbonylphenyl, or 4-loweralkoxycarbonylphenyl), benzoyl, amino, —NHR³ (where R³ is —C(NH)NH₂, C(O)NH-loweralkyl or phenyl, phenyl, loweralkylcarbonylphenyl or benzenesulfonyl), benzenesulfonyl, benzenesulfinyl, benzenesulfenyl, —CH₂CH(OH)CH₂OC₆H₅, phenylaminocarbonyl, or loweralkylaminocarbonyl;
R² is H, loweralkyl, phenyl or phenyl substituted by halogen, loweralkyl, loweralkoxy, trifluoromethyl, loweralkylcarbonyl, or diloweralkylaminoloweralkyl; with a proviso that when—(Q)ₙAr is —CH₂C₆H₅ or —CH₂CH=CHC₆H₅, X cannot be H and W cannot be 1-methyl-4-piperidinyl; the stereoisomers thereof; or pharmaceutically acceptable acid addition salts thereof.

2. Compounds of claim 1 which are
N,α-bis(4-fluorophenyl)-4-piperidinemethanamine,
1-[4-[3-[4-[(4-fluorophenyl)][(4-fluorophenyl)amino]methyl]-1-piperidinyl]propoxy]-3-methoxyphenyl]ethanone,
4-[(4-fluorophenyl)[(4-fluorophenyl)amino]methyl]-1,1-bis(3-phenyl-2-propenyl)piperidinium chloride,
N,α-bis(4-fluorophenyl)-1-(1-methylethyl)-4-piperidinemethanamine,
N,α-bis(4-fluorophenyl)-1-(3-phenyl-2-propenyl)-4-piperidinemethanamine,
4-[(4-fluorophenyl)[(4-fluorophenyl)amino]methyl]-α-(phenoxymethyl)-1-piperidineethanol,
N,α-bis(4-fluorophenyl)-1-(3-phenoxypropyl)-4-piperidinemethanamine,
4-[(4-fluorophenyl)[(4-fluorophenyl)amino]methyl]-N-methyl-1-piperidinecarboxamide,
4-[(4-fluorophenyl)[(4-fluorophenyl)amino]methyl]-N-phenyl-1-piperidinecarboxamide,
N,α-bis(4-fluorophenyl)-1-(4-phenylbutyl)-4-piperidinemethanamine,
N-[[1-[3-(4-acetyl-2-methoxyphenoxy)propyl]-4-piperidinyl](4-fluorophenyl)methyl]-N-(4-fluorophenyl)acetamide,
1-[3-[4-(1,1-dimethylethyl)phenoxy]propyl]-N,α-bis(4-fluorophenyl)-4-piperidinemethanamine,
4-[3-[4-[(4-fluorophenyl)][(4-fluorophenyl)amino]methyl]-1-piperidinyl]propoxy]benzoic acid 1,1-dimethylethyl ester,
N,α-bis(4-fluorophenyl)-1-(2-naphthalenylmethyl)-4-piperidinemethanamine,
N,α-bis(4-fluorophenyl)-1-[2-(2-naphthalenyloxy)ethyl]-4-piperidinemethanamine,
N,α-bis(4-fluorophenyl)-1-(phenylmethyl)-4-piperidinemethanamine,
1-[4-[3-[4-[(4-fluorophenyl)][(4-fluorophenyl)amino]methyl]-1-piperidinyl]propoxy]phenyl]-2-methyl-1-propanone,
1-cyclohexyl-N,α-bis(4-fluorophenyl)-4-piperidinemethamine,
N,α-bis(4-fluorophenyl)-1-(2-methylpropyl)-4-piperidinemethanamine,
N,α-bis(4-fluorophenyl)-1-propyl-4-piperidinemethanamine,
1-(2-ethoxyethyl)-N,α-bis(4-fluorophenyl)-4-piperidinemethanamine,
4-[[(3,4-difluorophenyl)amino](4-fluorophenyl)methyl]-piperidine,
N-(3,4-difluorophenyl)-α-(4-fluorophenyl)-1-(3-phenoxypropyl)-4-piperidinemethanamine,
N-(3,4-difluorophenyl)-α-(4-fluorophenyl)-1-(2-naphthalenylmethyl)-4-piperidinemethanamine,
N-(3,4-difluorophenyl)-α-(4-fluorophenyl)-1-[2-(2-naphthalenyloxy)ethyl]-4-piperidinemethanamine,
α-(4-fluorophenyl)-N-[(4-fluorophenyl)methyl]-4-piperidinemethanamine,
α-(4-fluorophenyl)-N-[(4-fluorophenyl)methyl]-1-(2-phenylethyl)-4-piperidinemethanamine,
N-[(4-fluorophenyl)methyl]-N-[(4-fluorophenyl)[1-(2-phenylethyl)-4-piperidinyl]methyl]acetamide,
N-[(4-fluorphenyl)methyl]-N-[(4-fluorophenyl)[1-(2-phenylethyl)-4-piperidinyl]methyl]-N-methylurea,
α-(4-fluorophenyl)-N-[(4-fluorophenyl)methyl]-1-(3-phenoxypropyl-4-piperidinemethanamine, 1-[4-[3-[4-[(4-fluorophenyl)[[(4-fluorophenyl)methyl-]amino]methyl]-1-piperidinyl]propoxy]-3-methoxyphenyl]ethanone, 4-[(4-fluorophenyl)[[(4-fluorophenyl)methyl]amino]methyl]-N-methyl-1-piperidinecarboxamide, N-[(4-fluorophenyl)methyl]-N-[(4-fluorophenyl)[1-[(methylamino)carbonyl]-4-piperidinyl]methyl]-N'-methylurea, N-[(4-fluorophenyl)methyl]-N-[(4-fluorophenyl)[1-(3-phenoxypropyl)-4-piperidinyl]methyl]acetamide, N-[(4-fluorophenyl)methyl]-N-[(4-fluorophenyl)[1-[(phenylamino)carbonyl]-4-piperidinyl]methyl]-N'-phenylurea, N-(3,4-difluorophenyl)-α-(4-fluorophenyl)-1-[3-(2-naphthalenyloxy)propyl]-4-piperidinemethanamine, N-(3,4-difluorophenyl)-α-(4-fluorophenyl)-1-[2-(1-naphthalenyloxy)ethyl]-4-piperidinemethanamine and N-(3,4-difluorophenyl)-α-(4-fluorophenyl)-1-(2-phenoxyethyl)-4-piperidinemethanamine;

the stereoisomers thereof and the pharmaceutically acceptable acid addition salts.

3. A method of treating warm blooded animals for angina which comprises administering thereto a therapeutically effective amount of a compound selected from the group having the formula

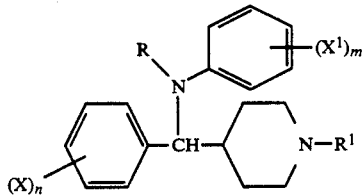

wherein

R is selected from H, loweralkyl, $R^2C(O)$—$R^2OC(O)$—, $R^2NHC(O)$—, or $(R^2)^2NC(O)$—;

m=0-2;

X and X' are independently selected from halogen, loweralkyl, trifluoromethyl, or —$OR^2$;

$R^1$ is selected from hydrogen, loweralkyl, loweralkylene, cycloloweralkyl, loweralkylcycloloweralkyl, $CF_3CH_2$—, or -(alk)p—Y where p is 0 or 1, alk refers to hydrocarbon radical, straight or branched, of from one to six carbons and may include one or more double bonds, and Y is —C(O)$NHR_2$, —C(NH)$NH_2$, phenyl, naphthyl, hydroxy, loweralkoxy, loweralkyleneoxy, aryloxy (where aryl is phenyl, naphthyl, 2-methoxy-4-acetylphenyl, 4-loweralkylcarbonylphenyl, or 4-loweralkoxycarbonylphenyl), benzoyl, amino, —$NHR^3$ (where $R^3$ is —C(NH)$NH_2$, C(O)NH-loweralkyl or phenyl, phenyl, loweralkylcarbonylphenyl or benzenesulfonyl), benzenesulfonyl, benzenesulfinyl, benzenesulfenyl, —$CH_2CH(OH)CH_2OC_6H_5$, phenylaminocarbonyl, or loweralkylaminocarbonyl;

$R^2$ is H, loweralkyl, phenyl or phenyl substituted by halogen, loweralkyl, loweralkoxy, trifluoromethyl, loweralkylcarbonyl, or diloweralkylaminoloweralkyl; with a proviso that when—$(Q)_nAr$ is —$CH_2C_6H_5$ or —$CH_2CH=CHC_6H_5$, X cannot be H and W cannot be 1-methyl-4-piperidinyl;

the stereoisomers thereof; or pharmaceutically acceptable acid addition salts thereof.

4. A pharmaceutical composition for treating warm-blooded animals for angina comprising:

a. a therapeutically effective amount of a compound selected from the group having the formula:

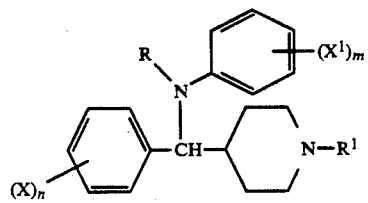

wherein

R is selected from H, loweralkyl, $R^2C(O)$—$R^2OC(O)$—, $R^2NHC(O)$—, or $(R^2)^2NC(O)$—;

m=0-2;

X and X' are independently selected from halogen, loweralkyl, trifluoromethyl, or —$OR^2$;

$R^1$ is selected from hydrogen, loweralkyl, loweralkylene, cycloloweralkyl, loweralkylcycloloweralkyl, $CF_3CH_2$—, or -(alk)p—Y where p is 0 or 1, alk refers to hydrocarbon radical, straight or branched, of from one to six carbons and may include one or more double bonds, and Y is —C(O)$NHR_2$, —C(NH)$NH_2$, phenyl, naphthyl, hydroxy, loweralkoxy, loweralkyleneoxy, aryloxy (where aryl is phenyl, naphthyl, 2-methoxy-4-acetylphenyl, 4-loweralkylcarbonylphenyl, or 4-loweralkoxycarbonylphenyl), benzoyl, amino, —$NHR^3$ (where $R^3$ is —C(NH)$NH_2$, C(O)NH-loweralkyl or phenyl, phenyl, loweralkylcarbonylphenyl or benzenesulfonyl), benzenesulfonyl, benzenesulfinyl, benzenesulfenyl, —$CH_2CH(OH)CH_2OC_6H_5$, phenylaminocarbonyl, or loweralkylaminocarbonyl;

$R^2$ is H, loweralkyl, phenyl or phenyl substituted by halogen, loweralkyl, loweralkoxy, trifluoromethyl, loweralkylcarbonyl, or diloweralkylaminoloweralkyl; with a proviso that when—$(Q)_nAr$ is —$CH_2C_6H_5$ or —$CH_2CH=CHC_6H_5$, X cannot be H and W cannot be 1-methyl-4-piperidinyl;

the stereoisomers thereof; or pharmaceutically acceptable acid addition salts thereof, and b. a pharmaceutically acceptable carrier.

* * * * *